(12) United States Patent
Amanullah

(10) Patent No.: US 9,816,938 B2
(45) Date of Patent: Nov. 14, 2017

(54) APPARATUS AND METHOD FOR SELECTIVELY INSPECTING COMPONENT SIDEWALLS

(71) Applicant: Semiconductor Technologies and Instruments Pte Ltd., Singapore (SG)

(72) Inventor: Ajharali Amanullah, Singapore (SG)

(73) Assignee: SEMICONDUCTOR TECHNOLOGIES & INSTRUMENTS PTE LTD, Singapore (SG)

( * ) Notice: Subject to any disclaimer, the term of this patent is extended or adjusted under 35 U.S.C. 154(b) by 283 days.

(21) Appl. No.: 14/548,313

(22) Filed: Nov. 20, 2014

(65) Prior Publication Data
US 2015/0138341 A1    May 21, 2015

Related U.S. Application Data

(60) Provisional application No. 61/906,576, filed on Nov. 20, 2013.

(51) Int. Cl.
*G01N 21/88* (2006.01)
*H04N 5/225* (2006.01)
(Continued)

(52) U.S. Cl.
CPC ........ *G01N 21/8806* (2013.01); *H04N 5/2256* (2013.01); *G01N 21/9501* (2013.01);
(Continued)

(58) Field of Classification Search
CPC ......... G01N 21/8806; G01N 2201/062; G01N 2021/8812; G01N 2201/0634;
(Continued)

(56) References Cited

U.S. PATENT DOCUMENTS

| 5,452,080 A | 9/1995 | Tomiya |
| 2002/0085199 A1 | 7/2002 | Shires |

(Continued)

FOREIGN PATENT DOCUMENTS

| JP | 1144513 | 2/1999 |
| JP | 2004301574 | 10/2004 |

(Continued)

*Primary Examiner* — Thai Tran
*Assistant Examiner* — Nien-Ru Yang
(74) *Attorney, Agent, or Firm* — Horizon IP Pte. Ltd.

(57) ABSTRACT

A component inspection process includes positioning a component (e.g., a semiconductor component or other object) such that component sidewalls are disposed along an optical path corresponding to sidewall beam splitters configured for receiving sidewall illumination provided by a set of sidewall illuminators, and transmitting this sidewall illumination therethrough, toward and to component sidewalls. Sidewall illumination incident upon component sidewalls is reflected from the component sidewalls back toward the sidewall beam splitters, which reflect or redirect this reflected sidewall illumination along an optical path corresponding to an image capture device for sidewall image capture to enable component sidewall inspection. Sidewall illuminators and sidewall beam splitters can form portions of a five sided inspection apparatus that includes a brightfield illuminator, a darkfield illuminator, and an image capture beam splitter such that the five sided inspection apparatus is configurable for inspecting component bottom surfaces and/or component sidewalls in a selective/selectable manner.

28 Claims, 23 Drawing Sheets

(51) Int. Cl.
  *G01N 21/95* (2006.01)
  *H01L 21/66* (2006.01)
(52) U.S. Cl.
  CPC .............. *G01N 2021/8812* (2013.01); *G01N 2201/062* (2013.01); *G01N 2201/0634* (2013.01); *H01L 22/12* (2013.01)
(58) Field of Classification Search
  CPC ......... G06T 7/0008; G06T 2207/30148; G06T 2207/10152; H04N 5/2256
  USPC ........................................................ 348/126
  See application file for complete search history.

(56) References Cited

U.S. PATENT DOCUMENTS

| | | | | |
|---|---|---|---|---|
| 2005/0259863 | A1* | 11/2005 | Freifeld ............... | G01N 21/952 382/152 |
| 2007/0120977 | A1* | 5/2007 | Duquette ........... | H04N 13/0207 348/87 |
| 2010/0188499 | A1* | 7/2010 | Amanullah ........ | G01N 21/8806 348/87 |

FOREIGN PATENT DOCUMENTS

| | | |
|---|---|---|
| JP | 2006140391 | 6/2006 |
| JP | 2010126242 | 6/2010 |
| JP | 2010160168 | 7/2010 |
| JP | 2011080932 | 4/2011 |
| JP | 2012141192 | 7/2012 |
| WO | 2010059130 | 5/2010 |

\* cited by examiner

FIG. 6C
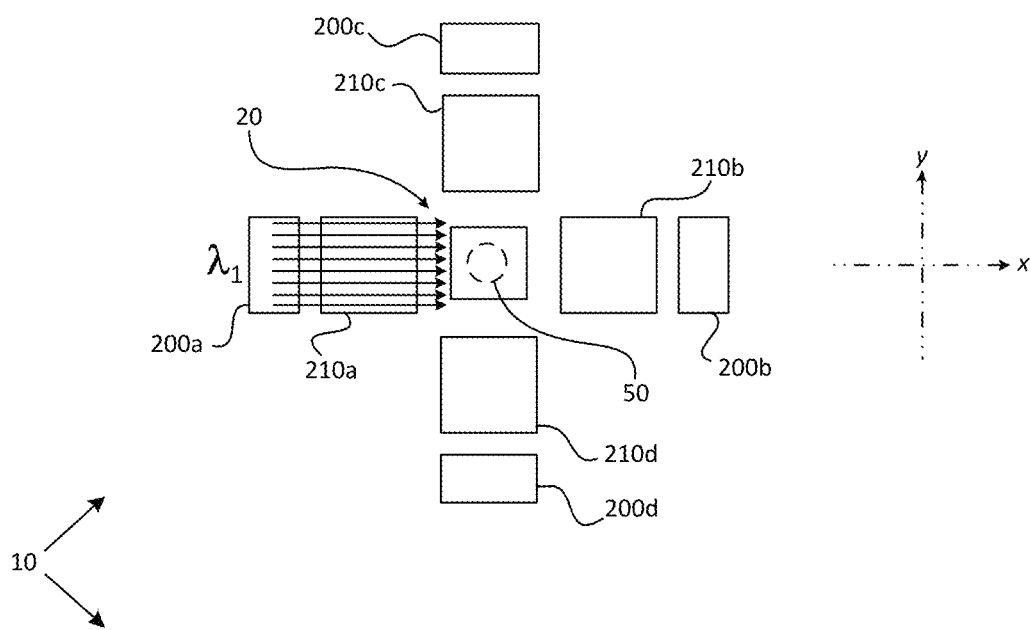
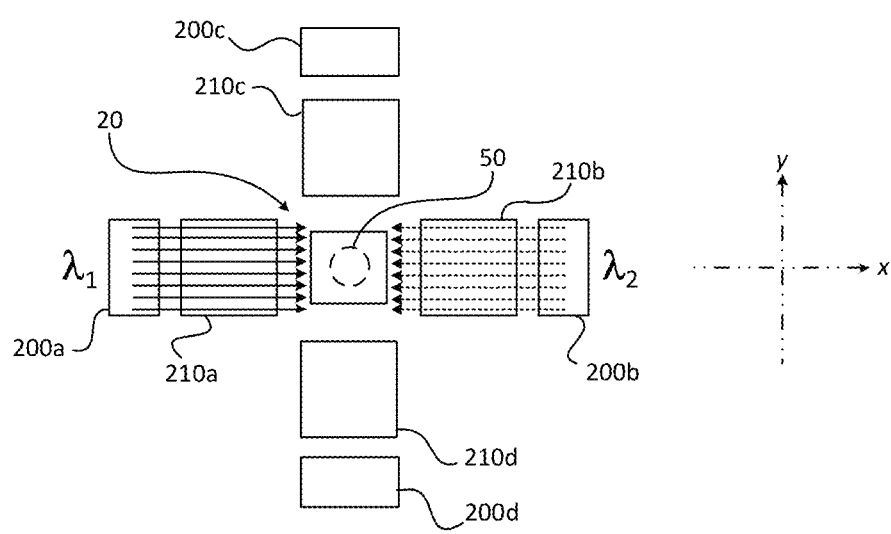
FIG. 6D

FIG. 6I
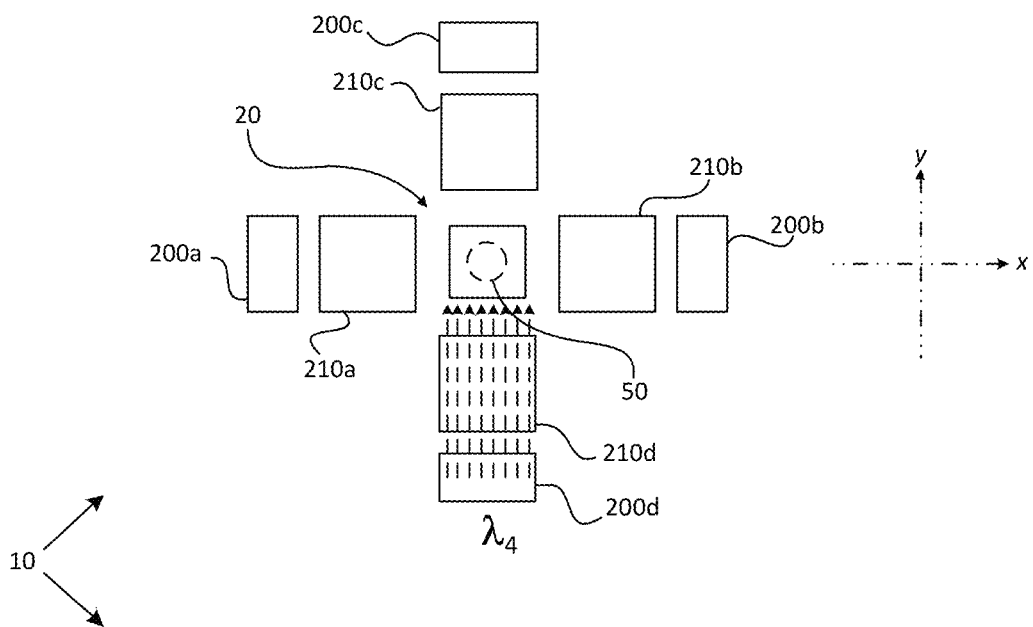
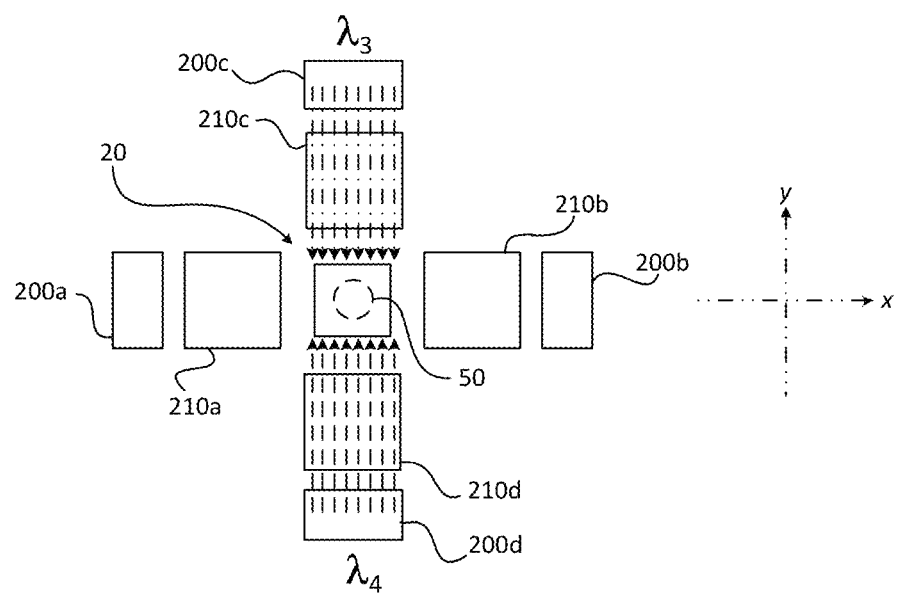
FIG. 6J

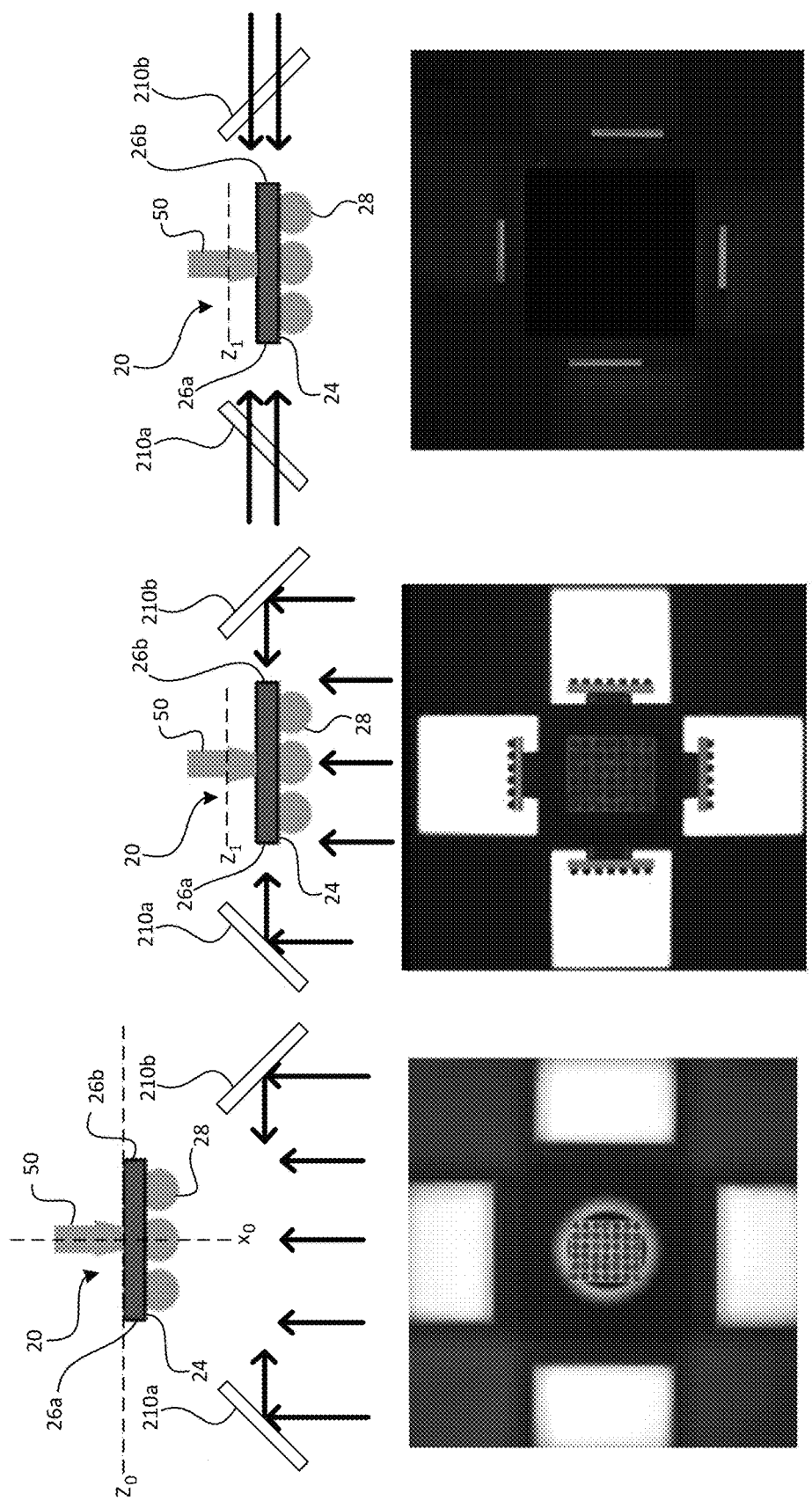

APPARATUS AND METHOD FOR SELECTIVELY INSPECTING COMPONENT SIDEWALLS

TECHNICAL FIELD

Aspects of the present disclosure are directed to apparatuses and methods for inspecting outer surfaces or sides of components, including component sidewalls, where sidewall inspection can occur in association with selectively directing illumination to some or all component sidewalls along optical travel paths such that the illumination is normally incident upon such sidewalls, and directing light reflected from the sidewalls such that an image capture device can capture sidewall images.

BACKGROUND

The optical inspection of external, exterior, or outer surfaces and/or structures of components such as semiconductor die or packaged semiconductor devices for defects can be performed by way of "five side inspection." Five side inspection involves directing illumination toward five sides of a component, such as a component bottom surface and four component sidewalls, when the component is held (e.g., by a pick and place device) on a sixth side, which in accordance with this definition of sides would be the component's bottom. In association with five side optical inspection, illumination can be directed to the component's bottom surface to facilitate the capture of a bottom surface image; and illumination can be directed to the component's sidewalls to facilitate the capture of component sidewall images. Incident illumination that is reflected from the component's bottom surface and/or sidewalls can be redirected toward an optical assembly such as a lens assembly and an image capture device for image capture purposes.

FIG. 1A is a schematic illustration showing portions of a conventional five side inspection apparatus, in which a component 20 is held by a component holder 50 (e.g., a pick-and-place device) in a bottom surface inspection position such that the component vertically resides at a bottom surface inspection position, above as well as between a set of reflectors or prisms 130a-b. While FIG. 1A illustrates only two prisms 130a-b, a typical five side inspection system includes four prisms 130, i.e., a prism corresponding to each of four sidewalls of the component.

A brightfield illuminator 100 outputs brightfield illumination in an upward direction, which passes through a beam splitter 110 as the brightfield illumination travels toward the component 20. Some of the brightfield illumination reaches and is reflected by a component bottom surface and/or surface features corresponding thereto, such as solder balls, and is directly reflected thereby in a downward direction toward the beam splitter 110. Upon reaching a reflecting surface 112 of the beam splitter, this downwardly traveling brightfield illumination is redirected toward an image capture device (not shown) such that an image corresponding to the component bottom surface can be captured.

Some of the brightfield illumination output by the brightfield illuminator 100 additionally reaches each prism 130a-b. Lateral optical paths between the prisms 130a-b are not blocked or obstructed by the component 20 because the component is disposed above the prisms 130a-b. Thus, upon reaching any given prism 130a-b, the brightfield illumination is redirected in a lateral direction toward an opposing prism 130b-a, after which the brightfield illumination is again redirected in a downward direction toward the beam splitter 110. Upon reaching the beam splitter's reflecting surface 112, this illumination which had travelled along an optical path through the prism 130a-b is further redirected toward an image capture device, and forms outer portions of the image captured thereby.

FIG. 1B is a representative inspection image corresponding to a component bottom surface captured while the component is held in a bottom surface inspection position corresponding to the inspection configuration shown in FIG. 1A. As indicated in FIG. 1B, brightfield illumination that had passed through the prisms 130a-b appears as bright or very bright peripheral portions of the captured image, and the component's bottom surface and structures corresponding thereto appear within an in-focus central region of the captured image.

After image capture is has occurred when the component is held at the bottom surface inspection position, the component holder 50 vertically lowers or plunges the component 20 to a sidewall inspection position, such that the component 20 resides between the prisms 130a-b and the component's sidewalls fall within the lateral optical paths between the prisms 130a-b. Thus, when the component is disposed at the sidewall inspection position, the component 20 acts as an obstruction relative to some illumination traveling from one prism 130a-b toward the other prism 130b-a.

More particularly, FIG. 1C is a schematic illustration showing portions of the conventional five side inspection apparatus, in which the component 20 is held by the component holder 50 at a sidewall inspection position, such that the component's vertical extent or height/thickness falls within the bounds of the vertical extent or height of the prisms 130a.b. As before, when the brightfield illuminator 100 outputs brightfield illumination, the brightfield illumination passes through a beam splitter 110 as the brightfield illumination travels in an upward direction toward the component 20. Some of the brightfield illumination reaches and is reflected by the component's bottom surface and/or surface features corresponding thereto, such as solder balls, and is directly reflected thereby in a downward direction toward the beam splitter 110. Upon reaching a reflecting surface 112 of the beam splitter 110, this downwardly traveling illumination corresponding to the component bottom surface is redirected toward an image capture device.

Some of the upwardly traveling brightfield illumination additionally reaches the set of prisms 130a-b. The prisms 130a-b reflect and redirect this brightfield illumination such that is travels laterally toward the component sidewalls. A portion of this laterally traveling illumination is reflected by the component sidewalls back toward the prisms 130a-b, which then reflect and redirect this illumination in a downward direction to the beam splitter 110, whereupon the beam splitter's reflecting surface 112 redirects this illumination that has been reflected by the component sidewalls toward the image capture device, such that images corresponding to each of the component's sidewalls can be captured, simultaneous with the capture of illumination corresponding to the component bottom surface/bottom surface structures while the component is positioned at the sidewall inspection position.

FIG. 1D is a representative inspection image captured while a component 20 is held at a sidewall inspection position, in which a central image region corresponds to brightfield illumination reflected by the component's bottom surface and/or structures carried thereby, and individual image regions at the left, right, bottom, and bottom of the image correspond to the component's sidewalls.

The image that is captured while the component 20 is held at the bottom surface inspection position provides a central in-focus image region corresponding to the component's bottom surface, and provides bright peripheral regions that contain or convey essentially no useful information about the component's sidewalls. The image that is captured while the component 20 is held at the sidewall inspection position provides in-focus peripheral image regions corresponding to the component sidewalls, and an at least slightly defocused central image region corresponding to the component bottom surface. This defocusing of the central image region within the image captured while the component 20 is held at the sidewall inspection position occurs as a result of the vertical offset between the bottom surface inspection position and the sidewall inspection position.

In particular, the vertical offset between the bottom surface inspection position and the sidewall inspection position is selected such that optical path lengths between the component's front surface and/or structures carried thereby (e.g., solder balls) and the image capture device's imaging plane are equal or approximately equal to optical path lengths between the component's sidewalls and the image capture device's imaging plane. As a result, no (re)focusing operation needs to occur between the capture of an image when the component 20 is plunged from the bottom surface inspection position to the sidewall inspection position, which aids inspection throughput.

For inspection purposes, a single composite image is typically created from the image captured while the component 20 was held at the bottom surface inspection position and the image captured while the component 20 was held at the sidewall inspection position. This composite image is generated by way of combining or digitally "stitching" together (a) the in-focus central region of the image captured while the component 20 was held at the bottom surface inspection position, corresponding to the component bottom surface, with (b) the in-focus peripheral or outer regions of the image captured while the component 20 was held at the sidewall inspection position, corresponding to the component sidewalls. FIG. 1E provides a representative composite image generated by way of combining or digitally stitching together central and peripheral portions of the bottom surface inspection image and the sidewall inspection image, respectively. FIG. 1F illustrates a portion of the composite image corresponding to a component sidewall.

In a conventional five side inspection apparatus, the vertical extent of the prisms 130 significantly exceeds the vertical extent of the component's sidewalls. Consequently, when a component 20 is positioned at the sidewall inspection position, upwardly traveling brightfield illumination output by the brightfield illuminator 100 which is incident upon the prisms 130 and which is directed or reflected by the prisms 130 toward the component sidewalls is vertically distributed across a spatial extent or area greater or significantly greater than the vertical extent of the component's sidewalls. Thus, a significant amount of brightfield illumination output by the brightfield illuminator 100 which has been redirected along a lateral path by a given prism 130 does not fall upon a component sidewall, and thus misses or bypasses the component entirely. Such brightfield illumination simply travels unobstructed to an opposite prism 130, and is reflected along a downward path to the beam splitter 110 whereupon it forms a portion of a captured image in which this brightfield illumination that had followed a direct prism-to-prism optical path appears as a brightly lit white background against the captured image of the component sidewalls, as indicated in FIG. 1D.

Such brightfield illumination that was directed along a lateral optical path perpendicular to a component sidewall, but was never incident upon component sidewalls and which instead simply experienced multiple prism reflections along optical paths that did not involve reflection from the component itself or structures associated therewith carries no optical information regarding component defects. Such illumination can therefore be referred to as extraneous brightfield illumination. This extraneous brightfield illumination is sufficiently intense or bright that its presence in a captured sidewall image can give rise to "optical crosstalk" that can visually "wash out" the appearance of shadows or very small defects (e.g., micro-defects such a hairline cracks or fractures) in sidewall images, thereby interfering with or limiting the extent to which image processing algorithms can detect micro-defects on component sidewalls. In other words, this extraneous brightfield illumination can decrease the contrast and sharpness of captured sidewall images. This is extremely significant since integrated circuits are increasingly getting smaller, and associated defects are also smaller, thereby increasing the need for improved image contrast and sharpness. Optical crosstalk tends to reduce the visibility and optical resolution or clarity of very small cracks (e.g., especially cracks having a size or dimension of less than or equal to approximately 10 μm).

A need exists for improving the manner in which component sidewalls are illuminated and component sidewall images are captured in five side inspection apparatuses.

SUMMARY

An aspect of the present disclosure is directed to a multi-side inspection apparatus, which can capture images of a component bottom surface and/or component sidewalls, where the apparatus is configured for inspecting component surfaces including component sidewalls, the apparatus including: a set of sidewall illuminators configured to output sidewall illumination; a set of sidewall beam splitters configured for: (a) receiving sidewall illumination output by the set of sidewall illuminators; (b) transmitting said sidewall illumination output by the set of sidewall illuminators through the set of sidewall beam splitters, such that at least some the sidewall illumination is incident on component sidewalls when a component is positioned at a sidewall inspection position at which the component sidewalls obstruct at least some optical paths between individual sidewall beam splitters within the set of sidewall beam splitters; (c) receiving reflected sidewall illumination from component sidewalls when the component is positioned at the sidewall inspection position; and (d) redirecting the reflected sidewall illumination along optical paths corresponding to a lens assembly and an image capture device.

Another important aspect of the present disclosure is directed to methods of eliminating the extraneous illumination crossing from one sidewall beam splitter on one side of the component to the sidewall beam splitter on the opposite side of the component that contributes to crosstalk and which tends to lessen the visibility of details and clarity of ultrafine defects in the sidewall images of component captured. Many of the embodiments use different techniques to eliminate extraneous light that contributes to crosstalk in component sidewall images.

In one embodiment, a method to eliminate crosstalk includes the use of suitable polarizer or combination of polarizers coupled to each pair of opposite sidewall beam splitters and configured using techniques known in the art such that (i) while each polarized beam splitter assembly (combination of set of polarizers and beam splitter) at one side of the component sidewall will allow illumination generated by its corresponding sidewall illuminators to pass through with a particular directional polarization, the direction of polarization of illumination passing through each of the pair of opposing beam splitter is different (ii) the polarized illumination through a polarized beam splitter from one side of the component (not reflected or blocked by the sidewall of the component) and passing over the component to the opposing polarized beam splitter assembly at the opposite side of the component would be absorbed or directed away by the said polarized beam splitter assembly. The result is that each of the opposite sidewalls of a component will be illuminated by light of different directional polarization and the extraneous polarized illumination not blocked by the component sidewall and passing over to the polarized beam splitter assembly at the opposite side of the component will be absorbed or eliminated by the receiving polarized beam splitter. This arrangement can apply to the each pair of opposite beam splitters so that a multi-side wall image of a component can be captured without crosstalk.

In an embodiment, the apparatus includes at least one pair of sidewall illuminators wherein two sidewall illuminators are oppositely disposed relative to each other with respect to the sidewall inspection position. Additionally or alternatively, the of sidewall beam splitters includes at least one pair of sidewall beam splitters that are oppositely disposed on different sides of the sidewall inspection area relative to an axis defined through the sidewall inspection area. The at least one pair of oppositely disposed sidewall beam splitters can include a first sidewall beam splitter and a second sidewall beam splitter, where the first sidewall beam splitter is configured for transmitting first sidewall illumination having a first optical wavelength or a first optical bandwidth therethrough and the second sidewall beam splitter is configured for transmitting second sidewall illumination having a distinct second optical wavelength or a second optical bandwidth therethrough. The first sidewall beam splitter is configured for receiving and redirecting each of first reflected sidewall illumination from a first component sidewall and second extraneous sidewall illumination transmitted through the second sidewall beam splitter that has traveled across the sidewall inspection area, and the second sidewall beam splitter is configured for receiving and redirecting each of second reflected sidewall illumination from a second component sidewall and first extraneous sidewall illumination transmitted through the first sidewall beam splitter that has traveled across the sidewall inspection area, where the first and second component sidewalls respectively face the first and second sidewall beam splitters, and hence the first and second component sidewalls can be considered to be oppositely oriented or directed with respect to each other and the first axis.

The apparatus can include an image capture device configured for (a) capturing in a single image capture operation a single image comprising a first image region corresponding to the first reflected sidewall illumination and the second extraneous sidewall illumination, and a second image region corresponding to the second reflected sidewall illumination and the first extraneous sidewall illumination, and (b) generating image data corresponding to the single image; and a processing unit configured for processing the image data such that pixel values corresponding to the second extraneous sidewall illumination are digitally filtered from image data corresponding to the first image region, and pixel values corresponding to the first extraneous sidewall illumination are digitally filtered from image data corresponding to the second image region.

The set of sidewall illuminators can include a plurality of sidewall illuminators in which (a) each sidewall illuminator outputs illumination at the same optical center wavelength or bandwidth, or (b) a first subset of sidewall illuminators outputs illumination having a distinct optical center wavelength or bandwidth relative to illumination output by a second subset of sidewall illuminators. Sidewall illuminators can be simultaneously activatable; or particular subsets of sidewall illuminators within the set of sidewall illuminators can be selectively activatable for outputting sidewall illumination while other subsets of sidewall illuminators within the set of sidewall illuminators remain inactive. The apparatus can also include a brightfield illuminator and/or a darkfield illuminator configured for selectively directing illumination toward a bottom surface or the bottom surface and sidewalls of a component positioned at the sidewall inspection position, wherein the component sidewalls extend between the bottom surface and a bottom surface of the component.

The apparatus can include an image capture beam splitter configured for (a) receiving illumination output by the brightfield illuminator and passing brightfield illumination therethrough; (b) receiving reflected brightfield and/or reflected darkfield illumination from the component bottom surface and/or sidewalls; (c) receiving reflected sidewall illumination from component sidewalls which has been redirected by the set of sidewall beam splitters; and (d) redirecting received reflected illumination corresponding to (b) and (c) along optical paths toward a lens assembly.

The apparatus also includes an image capture device configured to receive illumination output by the lens assembly, where the image capture device can include a monochrome image sensor or a color image sensor.

The apparatus can also include a component holder configured for selectively positioning a component at the sidewall inspection position or a bottom-surface-only inspection position at which component obstruction of optical paths between each sidewall beam splitter is avoided. In an embodiment, the component holder is configured for selectively positioning a component held thereby at multiple sidewall inspection positions within an inspection area definable between a plurality of sidewall beam splitters, including a first sidewall inspection position at which a component center point is positioned closer to a first subset of sidewall beam splitters than a distinct second subset of sidewall beam splitters, and a second sidewall inspection position at which the component center point is positioned closer to the second subset of sidewall beam splitters than the first set of sidewall beam splitters.

The apparatus can include a control unit configured for selectively controlling activation of subsets of sidewall illuminators within the set of sidewall illuminators, positioning the component at one or more inspection positions within the inspection area, and capture of one or more images of component surfaces by way of the image sensor.

In accordance with an aspect of the present disclosure, a process for inspecting one or multiple sides of a component, such as component side surfaces/sidewalls, includes: providing a set of sidewall illuminators configured for outputting sidewall illumination at one or more center wavelengths or wavelength ranges; providing a set of sidewall beam splitters configured for receiving sidewall illumination output by the set of sidewall illuminators; disposing a component at a first sidewall inspection position such that component sidewalls at least partially obstruct at least some optical paths between individual sidewall beam splitters within the set of sidewall beam splitters; directing sidewall illumination output by the set of sidewall illuminators toward component sidewalls by way of passing sidewall illumination received by the set of sidewall beam splitters therethrough; receiving sidewall illumination output by the set of sidewall beam splitters at a plurality of component sidewalls while the component resides at the first sidewall inspection position; receiving reflected sidewall illumination from the plurality of component sidewalls at the plurality of sidewall beam splitters; and redirecting reflected sidewall illumination received by the plurality of sidewall beam splitters along optical paths corresponding to an image capture device.

The process can include selectively directing sidewall illumination toward a first subset of component sidewalls while avoiding directing sidewall illumination toward a second subset of component sidewalls during a first image capture operation; and/or selectively directing sidewall illumination toward the second subset of component sidewalls while avoiding directing sidewall illumination toward the first subset of component sidewalls during a second image capture operation.

The process can include capturing a first image (e.g., while the component is centrally disposed within the sidewall inspection area, or disposed a first sidewall inspection position within a sidewall inspection area definable between the set of sidewall beam splitters, which can be a first off-center sidewall inspection position) including pixel regions corresponding to a first subset of component sidewalls; and capturing a second image (e.g., while the component is centrally disposed within the sidewall inspection area, or disposed at a distinct second sidewall inspection position within the sidewall inspection area, which can be a second off-center sidewall inspection position) including pixel regions corresponding to a second subset of component sidewalls. When the component is disposed at the first sidewall inspection position, a center point of the component can be closer to a first subset of sidewall beam splitters; and when the component is disposed at the second sidewall inspection position, the center point of the component can be closer to a distinct second subset of sidewall beam splitters when the component is disposed at the second sidewall inspection position.

A composite image can be created by way of digitally stitching together portions of the first image corresponding to the first subset of component sidewalls and portions of the second image corresponding to the second subset of component sidewalls. Automated inspection operations can be performed on individual captured images, and/or a composite image.

Sidewall illumination can include first sidewall illumination and second sidewall illumination, and the reflected sidewall illumination can correspondingly include first reflected sidewall illumination and second reflected sidewall illumination, wherein the first sidewall illumination and the second sidewall illumination exhibit different bandwidth limited optical wavelength ranges, and/or the first reflected sidewall illumination and the second reflected sidewall illumination exhibit different bandwidth limited optical wavelength ranges. The process can include capturing as a single view an image (e.g., a single image captured in a single image capture operation) including a plurality of distinct pixel regions, each pixel region corresponding to a distinct component sidewall, each pixel region corresponding to one of at least two distinct bandwidth limited optical wavelength ranges.

The process can include performing a wavelength segregated calibration procedure prior to capturing the image, for determining at least one calibration factor that can be applied to a pixel region corresponding to a particular component sidewall to determine, reduce, eliminate, or effectively eliminate an effect of extraneous sidewall illumination in the captured image.

The process can also include capturing at least one image including pixel regions corresponding to at least two component sidewalls while the component resides at the sidewall inspection position; displacing the component to a bottom-surface-only inspection position at which component obstruction of optical paths between each sidewall beam splitter is avoided; directing brightfield and/or darkfield illumination toward a bottom surface of the component while the component resides at the bottom-surface-only inspection position; and capturing an image corresponding to the bottom surface of the component.

In accordance with an aspect of the present disclosure, a process for inspecting a component having a plurality of sidewalls including a first component sidewall and a second component sidewall that face an opposite direction relative to each other along a first axis includes: positioning the component at a sidewall inspection position within a sidewall inspection area between a plurality of sidewall beam splitters including a first sidewall beam splitter and a second sidewall beam splitter that are disposed on opposite sides of the sidewall inspection area along the first axis; simultaneously transmitting sidewall illumination through the plurality of sidewall beam splitters such that the first component sidewall and the second component sidewall receive first incident sidewall illumination and second incident sidewall illumination thereon, respectively, at different optical center wavelengths or different optical bandwidths; receiving at the first sidewall beam splitter (a) first reflected sidewall illumination traveling away from the first component sidewall after first incident sidewall illumination arrival thereon and reflection therefrom, and (b) second extraneous sidewall illumination that has been transmitted through the second sidewall beam splitter across the sidewall inspection area; receiving at the second sidewall beam splitter (c) second reflected sidewall illumination traveling away from the second component sidewall after second incident sidewall illumination arrival thereon and reflection therefrom, and (d) first extraneous sidewall illumination that has been transmitted through the first sidewall beam splitter across the sidewall inspection area; redirecting each of the first reflected sidewall illumination, the second extraneous sidewall illumination, the second reflected sidewall illumination, and the first extraneous sidewall illumination toward an image capture device; while the component is disposed at the sidewall inspection position, capturing in a single image capture operation as a single image the first reflected sidewall illumination and the second extraneous sidewall illumination as a first region of the single image, and the second reflected sidewall illumination and the first extraneous sidewall illumination as a second region of the single image; generating image data corresponding to the single image; and processing the image data to digitally filter pixel values corresponding to the second extraneous sidewall illumination from the first region of the single image, and digitally filter the first extraneous sidewall illumination from the second region of the single image.

Simultaneous with or separate from the preceding process, analogous, effectively/essentially identical process operations can be performed for transmitting third and fourth sidewall illumination through third and fourth sidewall beam splitters that are disposed on opposite sides of the sidewall inspection area relative to a distinct second axis, such that third and fourth component sidewalls which are oppositely disposed relative to each other along the second axis receive third and fourth incident sidewall illumination, respectively; receiving at the third sidewall beam splitter (a) third reflected sidewall illumination traveling away from the third component sidewall after third incident sidewall illumination arrival thereon and reflection therefrom, and (b) fourth extraneous sidewall illumination that has been transmitted through the fourth sidewall beam splitter across the sidewall inspection area; receiving at the fourth sidewall beam splitter (c) fourth reflected sidewall illumination traveling away from the fourth component sidewall after fourth incident sidewall illumination arrival thereon and reflection therefrom, and (d) third extraneous sidewall illumination that has been transmitted through the third sidewall beam splitter and which has traveled across the sidewall inspection area; redirecting each of the third reflected sidewall illumination, the fourth extraneous sidewall illumination, the fourth reflected sidewall illumination, and the third extraneous sidewall illumination toward the image capture device; while the component is disposed at the sidewall inspection position, capturing in a single view the third reflected sidewall illumination and the fourth extraneous sidewall illumination as a third region of the single view, and the fourth reflected sidewall illumination and the third extraneous sidewall illumination as a fourth region of the single view; generating image data corresponding to the single view; and processing the image data of the single view to digitally filter pixel values corresponding to the fourth extraneous sidewall illumination from the third region of the single view, and digitally filter the third extraneous sidewall illumination from the fourth region of the single view.

BRIEF DESCRIPTION OF THE DRAWINGS

FIG. 6C is a schematic illustration of a first sidewall illuminator activation pattern corresponding to a wavelength segregated sidewall inspection calibration procedure in accordance with an embodiment of the present disclosure.

FIG. 6D is a schematic illustration of a second sidewall illuminator activation pattern corresponding to a wavelength segregated sidewall inspection calibration procedure in accordance with an embodiment of the present disclosure.

FIG. 6I is a schematic illustration of a seventh sidewall illuminator activation pattern corresponding to a wavelength segregated sidewall inspection calibration procedure in accordance with an embodiment of the present disclosure.

FIG. 6J is a schematic illustration of a eighth sidewall illuminator activation pattern corresponding to a wavelength segregated sidewall inspection calibration procedure in accordance with an embodiment of the present disclosure.

FIGS. 7A-7C illustrate a representative component inspection positions and corresponding representative captured images associated with a bottom-surface-only inspection position and a sidewall inspection position in accordance with an embodiment of the present disclosure.

DETAILED DESCRIPTION

Figure 1A:
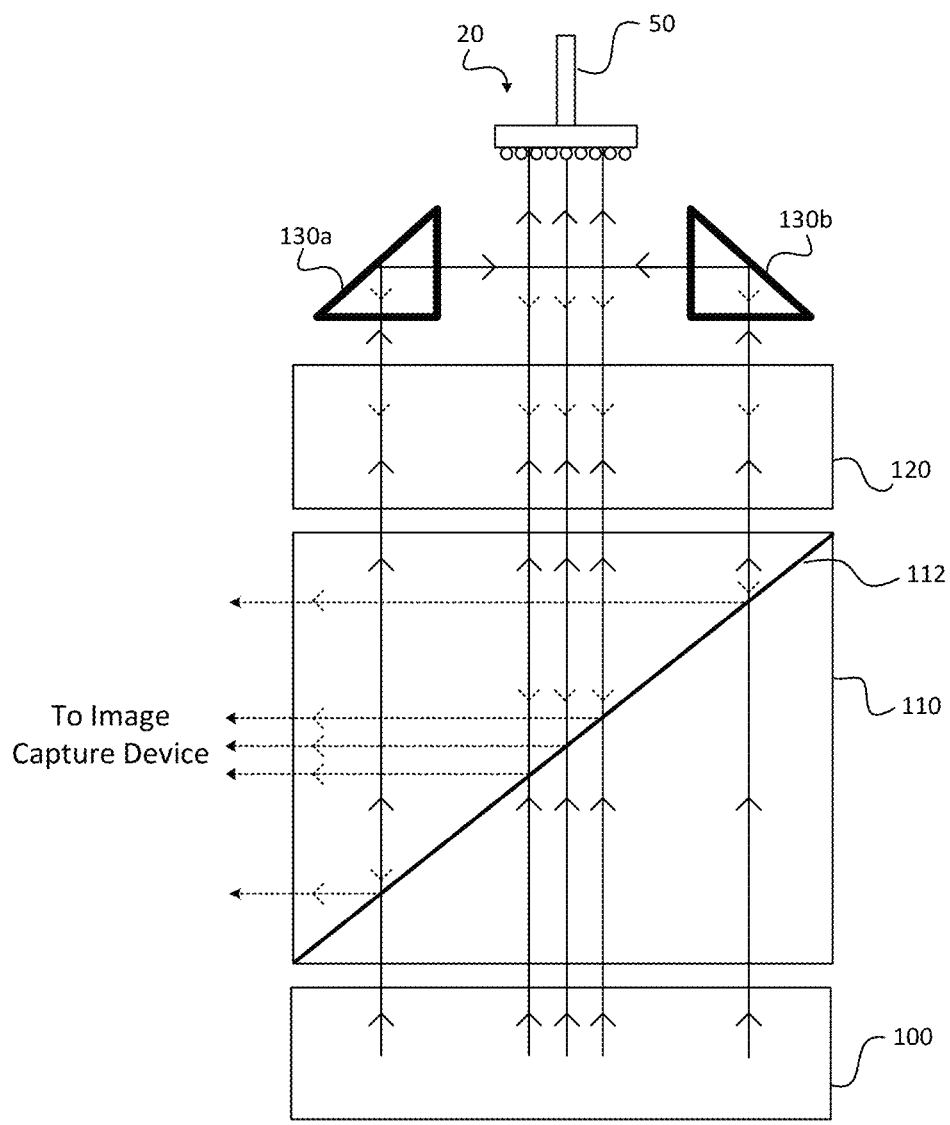
FIG. 1A is a schematic illustration showing portions of a conventional five side inspection apparatus.

In the present disclosure, depiction of a given element or consideration or use of a particular element number in a particular FIG. or a reference thereto in corresponding descriptive material can encompass the same, an equivalent, or an analogous element or element number identified in another FIG. or descriptive material associated therewith. The use of "/" in a FIG. or associated text is understood to mean "and/or" unless otherwise indicated. The recitation of a particular numerical value or value range herein is understood to include or be a recitation of an approximate numerical value or value range (e.g., within +/−20%, +/−15%, +/−10%, or +/−5%). Additionally, the use of "substantially perpendicular" or "generally perpendicular," can be taken to mean approximately perpendicular, e.g., perpendicular to within an angular extent of +/−10 degrees, or +/−5 degrees; and the use of "substantially parallel" or "generally parallel," can be taken to mean approximately parallel, e.g., parallel to within an angular extent of +/−10 degrees, or +/−5 degrees.

As used herein, the term "set" corresponds to or is defined as a non-empty finite organization of elements that mathematically exhibits a cardinality of at least 1 (i.e., a set as defined herein can correspond to a unit, singlet, or single element set, or a multiple element set), in accordance with known mathematical definitions (for instance, in a manner corresponding to that described in *An Introduction to Mathematical Reasoning: Numbers, Sets, and Functions*, "Chapter 11: Properties of Finite Sets" (e.g., as indicated on p. 140), by Peter J. Eccles, Cambridge University Press (1998)). In general, an element of a set can include or be a system, an apparatus, a device, a structure, an object, a process, a physical parameter, or a value depending upon the type of set under consideration.

Embodiments in accordance with the present disclosure are directed to systems, apparatuses, devices, structures, processes, and procedures for optically inspecting exposed, exterior, or outer surfaces of components, including component side surfaces that extend between (a) a top or upper boundary, border, or edge of a component or a point thereon, and (b) a bottom or lower boundary, border, or edge of the component or a point thereon, and possibly external component structures associated therewith. For purpose of simplicity and to aid understanding, component side surfaces are referred to herein as "sidewalls." Components can include, for instance, semiconductor devices such as semiconductor die or packaged integrated circuit (IC) chips, or other types of objects. Notwithstanding such nomenclature, it will be understood by one having ordinary skill in the relevant art based upon the description herein that embodiments in accordance with the present disclosure are applicable to the optical inspection of exposed, exterior, or outer component side surfaces in (a) situations in which such component side surfaces form one or more walls or wall-type structures, as well as (b) situations in which such component side surfaces do not form one or more walls or wall-type structures. More particularly, while various embodiments in accordance with the present disclosure are applicable to the optical inspection of regular or generally regular polyhedral components (e.g., components exhibiting a rectangular cuboid or generally rectangular cuboid shape) having outer side surfaces that correspond to well defined or readily identifiable vertical, angular, and/or angled outer/exterior walls or faces, multiple embodiments in accordance with the present disclosure are also applicable to the optical inspection of components exhibiting other types of shapes (e.g., components exhibiting an ellipsoidal or generally ellipsoidal shape) for which vertical, angular, or angled walls or faces are not necessarily well defined.

Depending upon embodiment details, embodiments in accordance with the present disclosure can be configured for inspecting component sidewalls and possibly structures associated therewith or projecting therefrom separately/apart from or in association with inspecting one or more other component surfaces, such as a component top surface and/or a component bottom surface and possibly structures associated therewith or projecting therefrom. Additionally, some embodiments are configured for the selective or selectable inspection of certain component sidewalls at a given time, and the inspection of other component sidewalls at another time. Certain embodiments are configured for the inspection of multiple subsets of component sidewalls simultaneously using sidewall illumination of multiple wavelengths or wavelength ranges, for instance, where a first subset of component sidewalls (e.g., a first pair of adjacent component sidewalls) is illuminated with sidewall illumination of a first optical wavelength or wavelength range, and another subset of component sidewalls (e.g., a second pair of adjacent component sidewalls) is concurrently illuminated with sidewall illumination of a different second optical wavelength or wavelength range. Inspection operations in accordance with embodiments of the present disclosure can occur under program control corresponding to the execution of program instruction sets/software by a processing unit. Such software can reside in a memory and/or upon a fixed or removable computer readable storage medium.

Figure 2A:
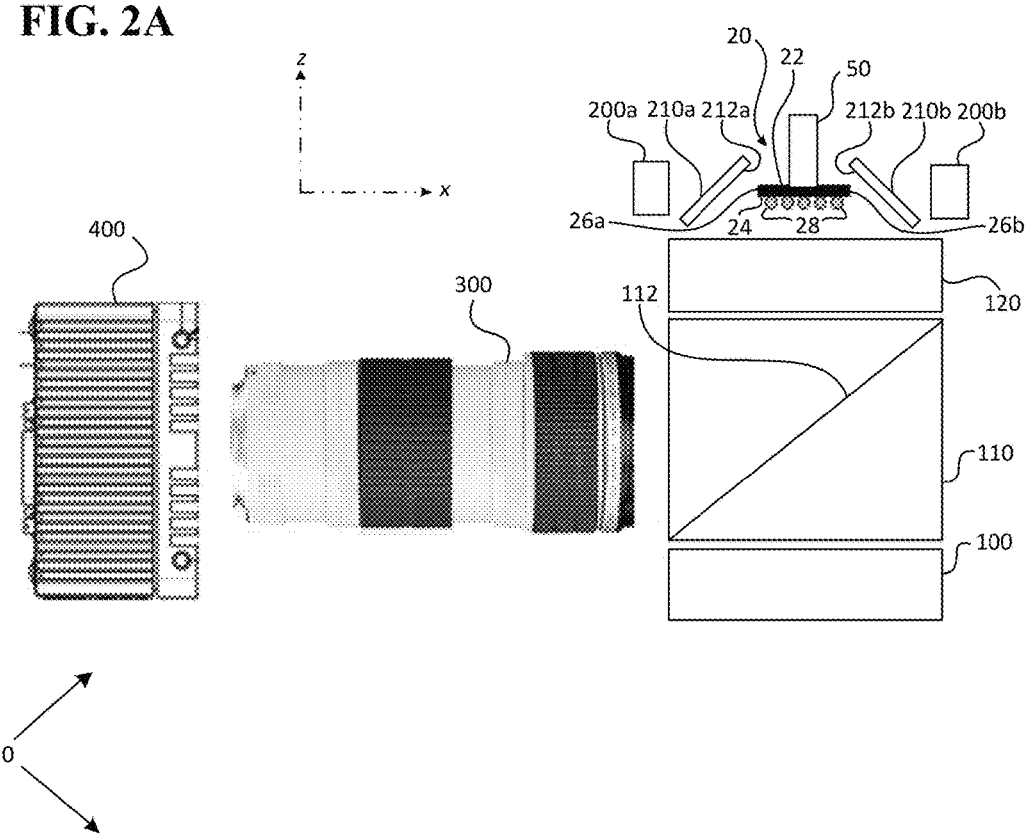
FIGS. 2A-2C illustrate portions of an apparatus configured for performing five sided component inspection as well as selective component sidewall inspection exclusive of component bottom or bottom surface inspection according to an embodiment of the present disclosure.
Figure 2B:
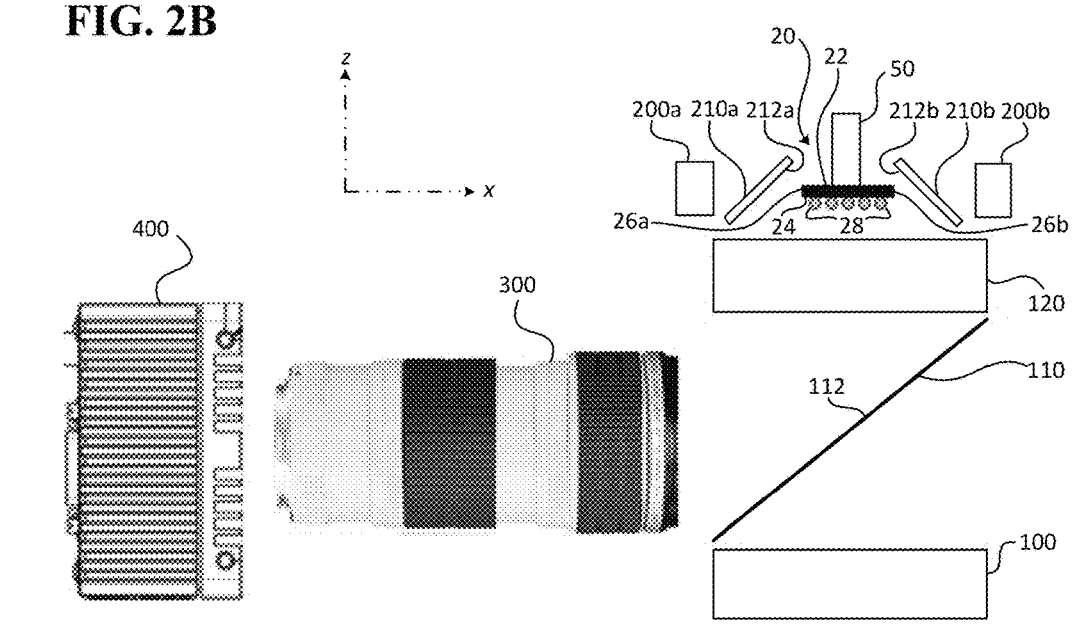
Figure 2C:
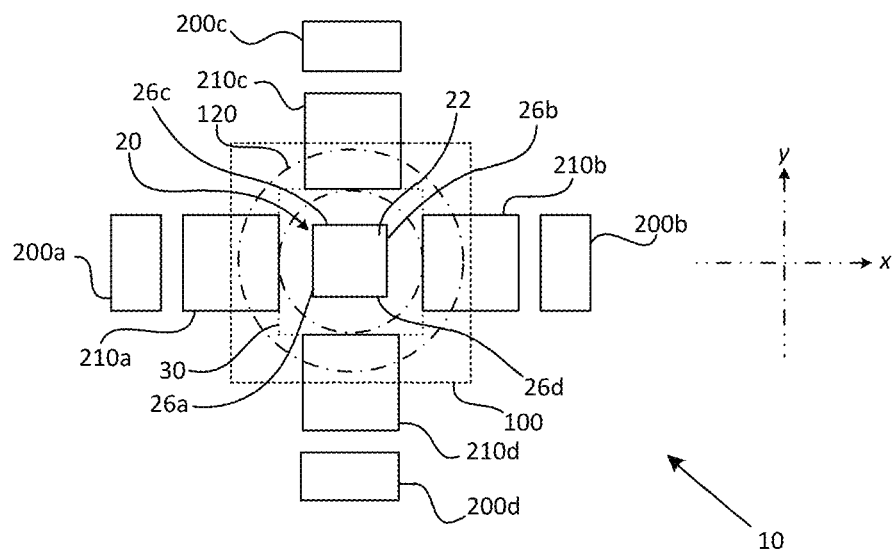

FIG. 2A is a schematic side view illustrating an apparatus 10 configured for (a) capturing images corresponding to up to five component sides, including images of a component bottom/front surface and/or component side surfaces/sidewalls; (b) facilitating or performing up to five sided component inspection; as well as (c) facilitating or performing component sidewall inspection (e.g., on a selective basis) exclusive of component bottom or bottom surface inspection according to an embodiment of the present disclosure. FIG. 2B is a schematic side view of the apparatus 10 in accordance with another embodiment of the present disclosure. FIG. 2C is a block diagram providing a top view of portions of the apparatus 10 of FIG. 2A and/or FIG. 2B in accordance with particular embodiments of the present disclosure. FIGS. 2A and 2B define an apparatus x axis and an apparatus z axis, and FIG. 2C further defines an apparatus y axis relative to the x axis, for spatial reference purposes.

Figure 2D:
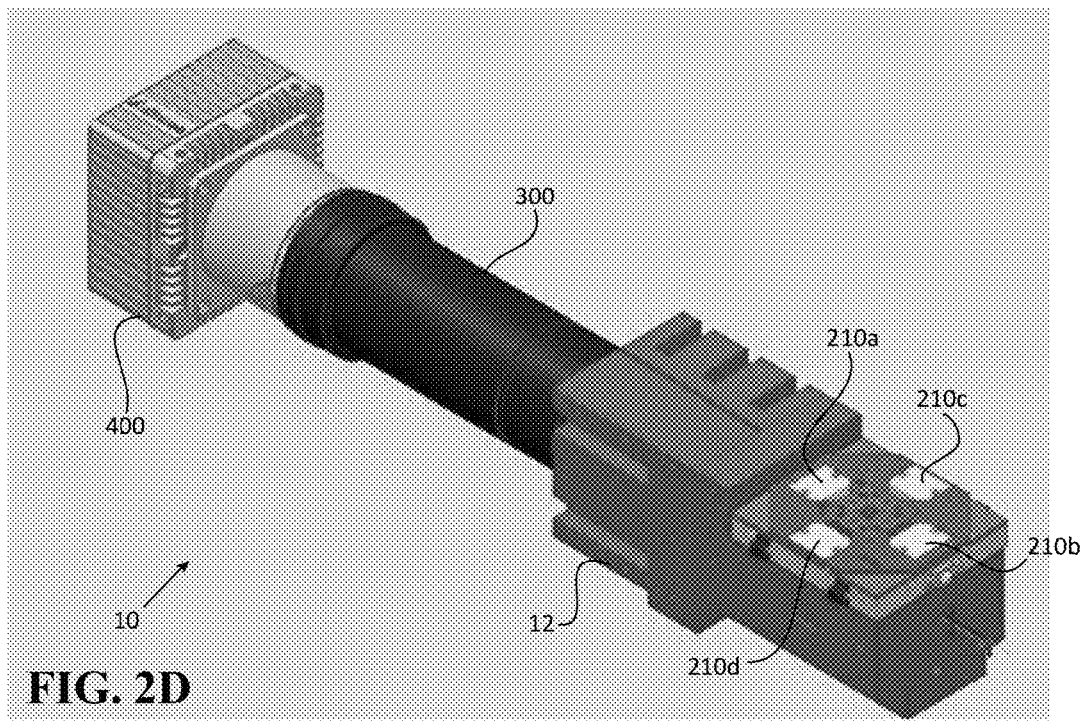
FIG. 2D illustrates a component disposed at a sidewall inspection position in accordance with an embodiment of the present disclosure.

In an embodiment, the apparatus 10 includes a component holder, holding structure, or retaining element 50 for securely holding or retaining a component 20 at one or more predetermined positions relative to each of a brightfield illuminator 100; an image capture beam splitter 110 (e.g., such as shown in FIGS. 2A, 2B, 3, and 4A); a darkfield illuminator 120; a set of sidewall illuminators 200, which in the embodiment shown includes an illumination setup, apparatus, or device having four distinct or distinguishable sidewall illumination output regions, or four distinct or distinguishable sidewall illuminators 200a-d; a set of sidewall beam splitters 210a-d; a lens assembly 300; and an image capture device 400 during a set or sequence of inspection operations. FIG. 2D is a schematic perspective view showing portions of the apparatus 10 of FIGS. 2A-2C, which indicates the apparatus 10 can include a housing 12 configured for carrying or supporting at least some of the image capture beam splitter 110, the set of sidewall beam splitters 210a-d, the set of sidewall illuminators 200a-d, the darkfield illuminator 120, and the brightfield illuminator 100, and portions of the lens assembly 300.

In the representative embodiment shown, the set of sidewall illuminators 200a-d includes a first through a fourth sidewall illuminator 200a-d; and the set of sidewall beam splitters correspondingly includes a first through a fourth sidewall beam splitter 210a-d. Other embodiments can include fewer or additional sidewall illuminators 200a-d and/or sidewall beam splitters 210a-d, depending upon embodiment details, component types under consideration, and/or component inspection requirements. Additionally, while each embodiment of an apparatus for selectively inspecting component sidewalls in accordance with the present disclosure includes a set of sidewall illuminators 200a-d and a corresponding set of sidewall beam splitters 210a-d, certain embodiments can omit the brightfield illuminator 100 and/or the darkfield illuminator 120.

In various embodiments, the set of sidewall illuminators 200 includes at least one illumination source. For instance, each sidewall illuminator 200a-d includes at least one illumination source, such as a set of LEDs (e.g., one or more sets of white light LEDs, and/or one or more sets of LEDs configured to output light at particular optical center wavelengths or optical bandwidths). Each sidewall beam splitter 210a-d can be a conventional beam splitter, such as a cube type beam splitter, a prism type beam splitter, a plate type beam splitter, or a mirror (e.g., a half-silvered mirror), which provides a beam splitting interface, surface, or face 212, such as a partially reflecting/partially transmitting interface or surface, at/along which beam splitting occurs in a manner readily understood by one having ordinary skill in the relevant art. Thus, each sidewall beam splitter 210a-d has associated therewith an illumination transmission direction and an illumination reflection direction, for instance, which is perpendicular to the illumination transmission direction. Illumination incident upon the sidewall beam splitter 210a-d along an optical path parallel to the illumination transmission direction travels through the sidewall beam splitter 210a-d with substantially or essentially no reflection; and illumination incident upon the sidewall beam splitter 210a-d along an optical path opposite to or opposing the transmission direction is reflected by the sidewall beam splitter 210a-d in the illumination reflection direction (e.g., perpendicular, essentially perpendicular, or substantially perpendicular to the illumination transmission direction), in a manner readily understood by an individual having ordinary skill in the relevant art.

Similarly, the image capture beam splitter 110 can be a conventional beam splitter, such as a cube type beam splitter, a prism type beam splitter, a plate type beam splitter, or a half-silvered mirror, which provides a beam splitting interface, surface, face 112 such as a partially reflecting/partially transmitting interface or surface at/along which beam splitting occurs, as readily understood by one having ordinary skill in the relevant art. The image capture beam splitter 110 thus has associated therewith an illumination transmission direction and an illumination reflection direction, for instance, which is perpendicular to the illumination transmission direction. Illumination incident upon the image capture beam splitter 110 along an optical path parallel to the illumination transmission direction travels through the image capture beam splitter 110 with essentially no reflection; and illumination incident upon the image capture beam splitter 110 along an optical path opposite to or opposing the illumination transmission direction is reflected by the image capture beam splitter 110 in the illumination reflection direction, as readily understood by an individual having ordinary skill in the relevant art.

The brightfield illuminator can be a conventional device configured for outputting brightfield illumination, and can include one or more illumination sources such as an array of LEDs (e.g., one or more sets of white light LEDs, and/or one or more sets of LEDs configured to output light at particular center wavelengths). The brightfield illuminator 100 can also be referred to as a brightfield co-axial illuminator, where "co-axial" is defined relative to the z axis, and indicates that the brightfield illuminator 100 is configured to output illumination in directions primarily or essentially parallel to the z axis. Correspondingly or equivalently, the brightfield illuminator 100 can be defined as or referred to as a brightfield unidirectional illuminator 100, indicating that the brightfield illumination output thereby propagates approximately, substantially, or essentially entirely in a single direction across a predetermined spatial distance, in a manner readily understood by one having ordinary skill in the relevant art. The darkfield illuminator can also be a conventional device configured for outputting high angle darkfield illumination and/or low angle darkfield illumination, such as a ring light that includes one or more rows or annular rings of LEDs.

The lens assembly 300 can include a conventional high resolution lens (e.g., a lens having a resolution of 2.0-4.0 microns), and the image capture device can be a conventional high resolution digital camera (e.g., a 25 megapixel camera).

In various embodiments, the component holder 50 includes or is a nozzle or tip corresponding to a pick-and-place apparatus (e.g., a conventional pick-and-place apparatus), which is configured to securely engage with a first surface 22 of a component 20 (e.g., by way of suction force) and carry or transport the component 20 to one or more inspection positions to facilitate inspection operations. For purpose of simplicity and to aid understanding, in the description herein the component holder 50 is defined to engage with the component 20 on the component's upper or top surface 22, such that a component second, bottom, or underside surface 24 is opposite to and faces away from the component's top surface 22. Brightfield illumination output by the brightfield illuminator 100 travels toward the bottom surface 24 of the component 20 along optical travel paths that are substantially or essentially perpendicular to the bottom surface 24 of the component 20. The component 20 includes a number of side surfaces or sidewalls 26, which in the representative embodiment shown includes or equals four sidewalls 26a-d, forming the component's outer periphery between the component's top and bottom surfaces 22, 24. The component 20 can be essentially any type of object or device for which inspection of images associated with or corresponding to its bottom surface 24 and/or some or all of its sidewalls 26a-d is desired or required. In the representative embodiment shown, the component 20 is an IC chip having a plurality of solder bumps or balls 28 on its bottom surface 24. One having ordinary skill in the relevant art will recognize that the manner engagement of the component holder 50 with the component 20 or a given component surface can vary or be changed, and/or the definitions of top/upper and bottom/underside surfaces 22, 24 can be reversed, depending upon embodiment and/or situational details. Such component engagement and component surface definitions are utilized herein purpose of example and to aid understanding.

In general, the component holder 50 can securely engage (e.g., in a releasable manner) with a given component's top surface 22, pick up the component 20, transport the component toward/to the apparatus 10, vertically position the component 20 along the z axis at one or more predetermined inspection positions relative to the apparatus 10, and laterally position the component 20 at one or more x-y plane positions within a sidewall inspection space, region, volume, or area 30 between the sidewall beam splitters 210a-d, such that (a) illumination can be directed to particular component surfaces using one or more of the brightfield illuminator 100, the darkfield illuminator 120, and the set of sidewall illuminators 200a-d, and (b) one or more images associated with or corresponding to the component's bottom surface 24 and/or one or more of the component's sidewalls 26a-d can be captured by way of (i) the reflection of illumination from such component surfaces 24, 26a-d, and (ii) the (re)direction of this reflected illumination toward and into the lens assembly 300 and to the image capture device 400.

In various embodiments, the component holder 50 can position a component 20 carried thereby at one or more sidewall inspection positions within the sidewall inspection area 30, at which the component 20 is disposed between the set of sidewall beam splitters 210a-d, and the component's sidewalls 26a-b are bordered, surrounded, or enclosed by the set of sidewall beam splitters 210a-d. For instance, the component holder 50 can position the component 20 at a centered or central sidewall inspection position, such that a midpoint, centroid, or center point of the component 20 resides approximately midway between the set of sidewall beam splitters 210a-d. For instance, while the component 20 is disposed at the centered sidewall inspection position, opposing or oppositely facing component sidewalls 26a,b, 26c,d can be approximately equidistant from corresponding opposing sidewall beam splitters 210a,b, 210c,d; or each component sidewall 26a-d can be approximately equidistant from a corresponding sidewall beam splitter 210a-d (e.g., depending upon the arrangement of sidewall beam splitters 210a-d, and the shape of the sidewall inspection area 30).

Additionally or alternatively, in some embodiments the component holder 50 can position a component 20 at an off-center sidewall inspection position, such that component sidewalls 26a,c-26b,d/26a,d-26b,c that share a common boundary or border (e.g., adjacent component sidewalls 26a,c-26b,d/26a,d-26b,c) are disposed equidistant from corresponding sidewall beam splitters 210a,c-210b,d/210a,d-210b,c (e.g., adjacent sidewall beam splitters 210a,c-210b, d/210a,d-210b,c) and the component midpoint, centroid, or center point is offset away from a midpoint between any two opposing or oppositely positioned sidewall beam splitters 210a,c-210b,d/210a,d-210b,c toward a corresponding selected/selectable subset of sidewall beam splitters 210a, c-210b,d/210a,d-210b,c (e.g., a given pair of adjacent sidewall beam splitters 210a,c-210b,d/210a,d-210b,c), whereby a particular subset of component sidewalls that share a common boundary or border 26a,c-26b,d/26a,d-26b.c (e.g., a particular pair of adjacent component sidewalls 26a,c-26b, d/26a,d-26b,c) is disposed closer to its corresponding selected/selectable subset of bordering or adjacent sidewall beam splitters 210a,c-210b,d/210a,d-210b,c than another subset of bordering or adjacent sidewall beam splitters 210a,d-210b,c/210a,c-210b,d. In such a situation, the sidewall illuminators 200a,c-200b,d/200a,d-200b,c corresponding to adjacent sidewall beam splitters 210a,c-210b,d/210a, d-210b,c can be selectively activated, and an image of corresponding component sidewalls 26a,c-26b,d/26a,d-26b,c that share a common boundary or border (e.g, adjacent component sidewalls 26a,c-26b,d/26a,d-26b,c) relative to the adjacent sidewall beam splitters 210a,c-210b,d/210a,d-210b,c under consideration can be captured, for instance, as a single image during a single image capture operation. The process can be repeated by moving or shifting the component 20 relative to or within the inspection area 30 to another off-center sidewall inspection position, for instance, in a diagonal direction away from a currently occupied corner region of the sidewall inspection area 30 to a currently unoccupied corner region of the sidewall inspection area 30, so that another pair of adjacent component sidewalls 26b, d-26a,c/26b,c-26a,d is disposed equidistant to corresponding bordering or adjacent sidewall beam splitters 210b,d-210a,c/210b,c-210a,d and the corresponding sidewall illuminators 200b,d-200a,c/200b,c-200a,d can be selectively activated and an image of the adjacent component sidewalls 26b,d-26a,c/26b,c-26a,d on which sidewall illumination is currently incident can be captured, for instance, as a single image during a single image capture operation.

This is further elaborated upon below with reference to a representative embodiment shown in FIGS. 5F and 5G.

In general, when the component 20 is disposed or held at a sidewall inspection position, the sidewall beam splitters 210a-d are disposed about portions of the component's periphery as defined by the surface area occupied by the component's sidewalls 26a-d, such that the vertical extent of each component sidewall 26a-d resides within the vertical extent of a corresponding sidewall beam splitter 210a-d. As a result, when the component 20 is disposed at a sidewall inspection position, the component 20 will act as an obstruction relative to the propagation of at least some light between pairs of oppositely disposed sidewall beam splitters 210a-d between which light can directly propagate in the absence of the component 20.

Figure 2E:
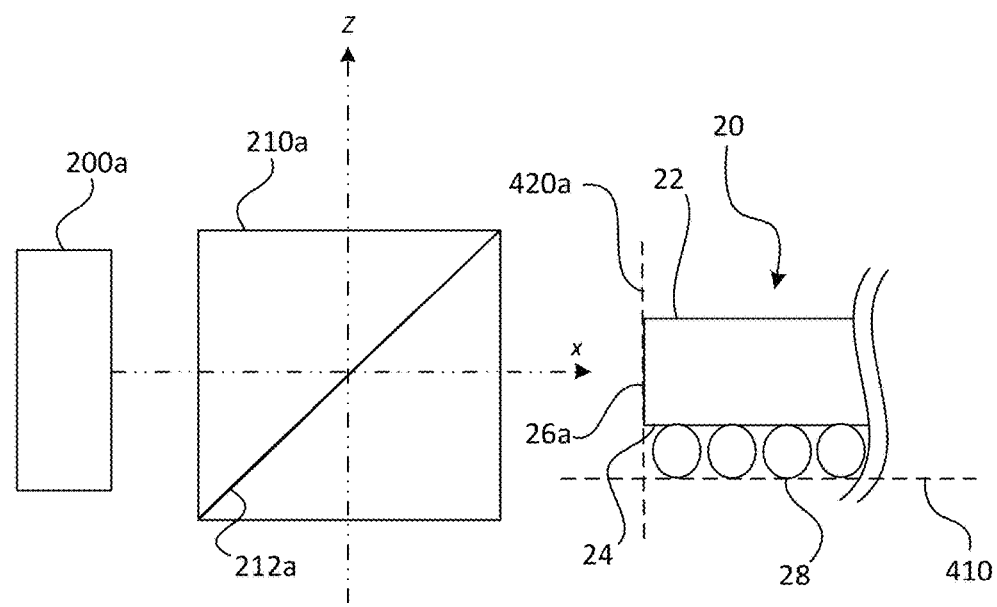
FIG. 2E is a schematic illustration showing a representative positioning of a component at a sidewall inspection position in accordance with an embodiment of the present disclosure.

FIG. 2E is a schematic illustration showing a representative positioning of a component 20 at a sidewall inspection position (e.g., a centered sidewall inspection position) in accordance with an embodiment of the present disclosure. More specifically, as indicated in FIG. 2E, when the component 20 is positioned at this representative sidewall inspection position, a first component sidewall 26a is positioned near or adjacent/proximate to a first sidewall beam splitter 210a, such that the first component sidewall 26a can receive illumination from the first sidewall beam splitter 210a at an angle of incidence of approximately 90 degrees. Still more particularly, the first sidewall 26a is disposed (a) perpendicular or substantially perpendicular to a first axis, such as the aforementioned x axis, which corresponds or is parallel to a first illumination propagation axis/optical axis and the illumination transmission direction of the first sidewall beam splitter 210a; and (b) parallel or substantially parallel to a second axis, such as a vertical or z axis, which corresponds or is parallel to a second illumination propagation axis/optical axis and the illumination reflection direction of the first sidewall beam splitter 210a.

Analogous considerations apply with respect to each of the component's second through fourth sidewalls 26b-d when the component resides at the sidewall inspection position shown in FIG. 2E. Therefore, when the component 20 is disposed at this sidewall inspection position, each of the component's first and second sidewalls 26a-b is disposed (a) perpendicular or substantially perpendicular to the aforementioned x axis, which corresponds or is parallel to a first illumination propagation axis/optical axis and the illumination transmission direction of each of the first sidewall beam splitter 210a and a second sidewall beam splitter 210b; and (b) parallel or substantially parallel to the aforementioned z axis, which corresponds or is parallel to a second illumination propagation axis/optical axis and the illumination reflection direction of each the first sidewall beam splitter 210a and the second sidewall beam splitter 210b. Additionally, each of the component's third and fourth sidewalls 26c-c is disposed (a) perpendicular or substantially perpendicular to the aforementioned y axis, which corresponds or is parallel to a first illumination propagation axis/optical axis and the illumination transmission direction of each of the third and fourth sidewall beam splitters 210c-d; and (b) parallel or substantially parallel to the aforementioned z axis, which corresponds or is parallel to a second illumination propagation axis/optical axis and the illumination reflection direction of each of the third and fourth sidewall beam splitters 210c-d.

While the component 20 is positioned at such a sidewall inspection position, the component 20 can obstruct illumination traveling along at least some optical paths parallel or substantially parallel to the x axis or the y axis between sidewall beam splitters 210a,b, 210c,d that are oppositely disposed relative to each other along the x axis or the y axis, respectively. Thus, the component's sidewalls 26a-d can be selectively/selectably illuminated by light incident thereupon as a result of (a) brightfield illumination output by the brightfield illuminator 100 and reflected by the set of sidewall beam splitters 210a-d towards the component sidewalls 26a-d; (b) darkfield illumination output by the darkfield illuminator 120, some of which will be directly incident upon the component sidewalls 26a-d and some of which will be reflected by the sidewall beam splitters 210a-d towards the component sidewalls 260a-d; and/or (c) sidewall illumination output by the set of sidewall illuminators 210 which has travelled through the set of sidewall beam splitters 210a-d along a direct optical path toward the component's sidewalls 26a-c. The likelihood of detecting particular types of defects present in or on component sidewalls 26a-d, especially very small or micro-defects, depends upon which of such illuminators is or are used when one or more images that include component sidewalls 26a-d are captured and subsequently processed/analyzed (e.g., by way of image processing operations), as further detailed hereafter.

In various embodiments, for each component sidewall 26a-d under consideration (e.g., each component sidewall 26a-d upon which sidewall illumination is incident), reflected sidewall illumination travels an equal distance between the component sidewall 26a-d and an image capture plane of the image capture device 400. Consequently, images of component sidewalls 26a-d that are captured while the component 20 is disposed at a sidewall inspection position within the sidewall inspection area 30 are in focus with respect to the image capture plane. Certain embodiments can include a number of optical elements disposed along optical paths between portions of the component 20 (e.g., component sidewalls 26a-d) and the image capture device 400 for purpose of compensating for optical path length differences between illumination reflected from the component bottom surface 24 and sidewall illumination reflected from the component sidewalls 26a-d relative to the image capture plane of the image capture device 400. For instance, referring to FIGS. 2B, 2C, and 2E, when the component 20 is centrally aligned relative to the sidewall beam splitters 210a-d such that the component 20 is disposed at a central sidewall inspection position within the sidewall inspection area 30, sidewall beam splitters 210a-d configured as prisms having appropriate refractive indices, and/or a set of prisms separate from the sidewall beam splitters 210a-d and which provide appropriate refractive indices, can be used to compensate for optical path length differences such that a bottom image plane 410 associated with or corresponding to the component's bottom surface 24 is in focus with respect to the image capture plane within the image capture device 400; and a first sidewall image plane 420a associated with or corresponding to the component's first sidewall 26a is in focus with respect to the image capture plane within the image capture device 400. Correspondingly, in such an embodiment, the bottom image plane 410, a second sidewall image plane corresponding to the component's second sidewall 26b, a third sidewall image plane corresponding to the component's third sidewall 26c, and a fourth sidewall image plane corresponding to the component's fourth sidewall 26d can each be in focus with respect to the image capture plane within the image capture device 400.

The image capture device 400 provides a field of view (FOV) that is sufficiently large to capture portions of the bottom image plane 410 and/or portions one or more sidewall image planes 420 by way of (a) separate image capture operations as separate images, or (b) a single image capture operation as a single image that includes pixels corresponding to imaged details of the component bottom surface 24 and/or pixels corresponding to imaged details of a given subset of component sidewalls 26a-d or each component sidewall 26a-d, depending upon embodiment details, a component inspection recipe under consideration (e.g., as defined by a set of program instructions executable by a processing unit), and/or a sidewall illuminator activation pattern under consideration.

Figure 3:
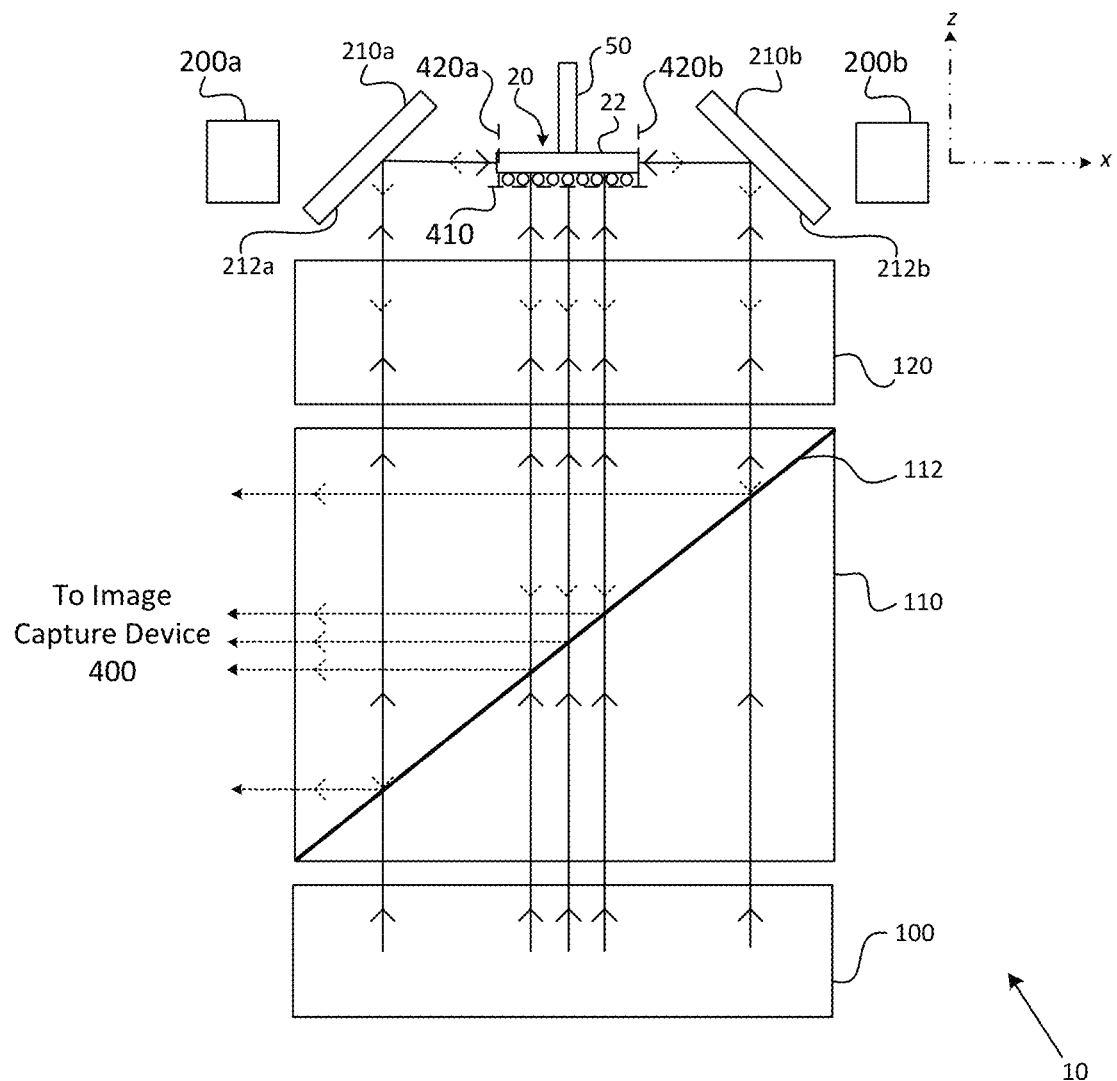
FIG. 3 is a schematic illustration showing representative illumination travel paths corresponding to component bottom surface inspection simultaneous with component sidewall inspection by way of a brightfield illuminator using the apparatus of FIGS. 2A-2C.

FIG. 3 is a schematic illustration showing a component 20 illuminated by brightfield illumination output by the brightfield illuminator 100 in accordance with an embodiment of the present disclosure, while the sidewall illuminators 200a-d are off, when the component 20 is positioned at the centered sidewall inspection position. In an embodiment, brightfield illumination emitted or output by the brightfield illuminator 100 includes illumination that travels along optical paths through the image capture beam splitter 110 along upward directions that are parallel or substantially/generally parallel to the z axis. Some of such brightfield illumination travels directly to the component's bottom surface 24 and the solder balls 28 disposed thereon. Brightfield illumination which is perpendicularly or approximately perpendicularly incident upon the component's bottom surface 24 and the solder balls 28 will be reflected thereby in downward directions that are parallel or substantially/generally parallel to the z axis, toward and to the image capture beam splitter's partially reflecting/partially transmitting surface 112, which subsequently reflects or redirects some of such reflected undersideside illumination toward and into the lens assembly 300, in directions parallel, substantially parallel, or generally parallel to the x axis.

Some of the brightfield illumination output by the brightfield illuminator 100 also travels upward along optical paths in directions parallel, substantially parallel, or generally parallel to the z axis to the sidewall beam splitters 210a-d, which reflect or redirect this brightfield illumination such that it travels along lateral optical paths that are parallel or substantially parallel to the x axis or the y axis, and perpendicular or substantially perpendicular to the component's sidewalls 20a-d. A portion of this laterally traveling illumination will be perpendicularly/substantially perpendicularly incident upon the component sidewalls 26a-d, and will be reflected thereby back toward the sidewall beam splitters 210a-d. The sidewall beam splitters 210a-d redirect this illumination received from the component sidewalls 26a-d in a downward direction toward the imaging beam splitter 110, and the imaging beam splitter's reflecting surface 112 redirects this illumination toward and into the lens assembly 300 and the image capture device 400.

Some of the aforementioned laterally traveling illumination reflected by the sidewall beam splitters 210a-d will not be incident upon the component sidewalls 26a-d or structures associated therewith (e.g., lead wires), and will simply travel past the component 20 to an opposite sidewall beam splitter 210a-d and be redirected toward the imaging beam splitter 110, whereupon this extraneous brightfield illumination is redirected toward and into the lens assembly 300 and the image capture device.

Thus, under brightfield illumination conditions, the apparatus 100 can behave as a conventional five side inspection apparatus, if such a mode of operation is desired or selected. Similar or generally similar considerations apply to darkfield illumination conditions and the generation of extraneous darkfield illumination, in a manner that an individual having ordinary skill in the relevant art will readily understand.

Representative Sidewall Illumination and Inspection Configurations/Operations

As further described in detail hereafter, various embodiments in accordance with the present disclosure can selectively disable, deactivate, or turn off the brightfield illuminator 100 and activate or turn on some or each of the sidewall illuminators 200a-d during an inspection process, such that extraneous brightfield illumination or the effect(s) thereof on sidewall inspection are compensated for or reduced, substantially eliminated, eliminated, or effectively/essentially eliminated from captured sidewall images. Similar considerations apply to turning off the darkfield illuminator 120 while some or each of the sidewall illuminators 200a-d remain active, such that extraneous darkfield illumination or the effect(s) thereof on sidewall inspection can be reduced, substantially eliminated, eliminated, or effectively/essentially eliminated from captured sidewall images. Furthermore, multiple embodiments in accordance with the present disclosure can de-activate the brightfield illuminator 100 and the darkfield illuminator 120 while selectively activating particular adjacent sidewall illuminators 200a,c, 200b,d (or 200a,d, 200b,c) during a sidewall inspection process while other sidewall illuminators remain inactive or off, to reduce, eliminate, or effectively/essentially eliminate (a) extraneous sidewall illumination arising from the transmission of sidewall illumination output by the set of sidewall illuminators 200a-d through oppositely disposed sidewall beam splitters 210a,b, 210c,d and across the sidewall inspection area 30 without reflection by component sidewalls 26a,b, 26c,d; and/or (b) the effect(s) of such extraneous sidewall illumination on sidewall inspection. Such extraneous sidewall illumination that arises from sidewall illumination output by the sidewall illuminators 200a-d during a component sidewall inspection procedure (e.g., during which the brightfield illuminator 100 and the darkfield illuminator 120 remain off) can be categorized or defined as non-brightfield extraneous illumination, and non-darkfield extraneous illumination. In various embodiments, extraneous sidewall illumination or the effects thereof on sidewall inspection can be compensated for or reduced, substantially eliminated, eliminated, or effectively/essentially eliminated by way of activating particular sidewall illuminators 200a-d or each sidewall illuminator 200a-d in an optical wavelength or optical bandwidth segregated manner relative to other sidewall illuminators 200a-d, and/or optical filtering based upon optical wavelengths or optical bandwidths associated with oppositely positioned sidewall illuminators 200a,b, 200c,d. Such sidewall illumination and inspection configurations and techniques can enhance or greatly enhance the contrast and sharpness of pixels within captured and/or composite images corresponding to component sidewalls, thereby enhancing or greatly enhancing the likelihood of detecting sidewall micro-defects (e.g., defects having a dimension of approximately 5 µm or less) and enhancing or greatly enhancing sidewall inspection accuracy.

Figure 4A:
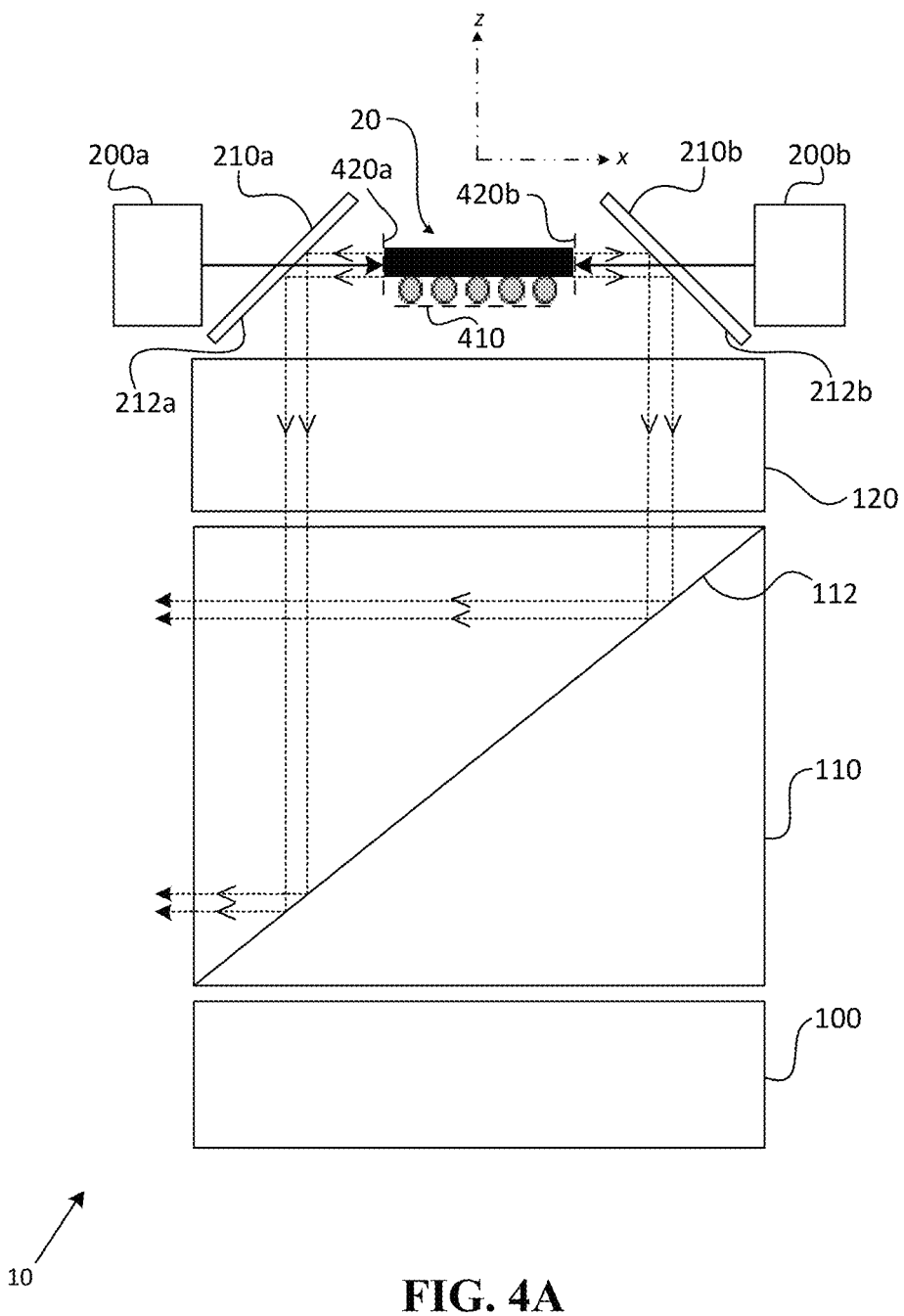
FIG. 4A is a schematic illustration showing representative illumination travel paths corresponding to selective component sidewall inspection exclusive of component bottom surface inspection by way of a set of sidewall illuminators using the apparatus of FIGS. 2A-2C.

FIG. 4A is a schematic illustration showing component sidewalls 26a-d illuminated by sidewall illumination output by the set of sidewall illuminators 200 in accordance with an embodiment of the present disclosure, while the brightfield and darkfield illuminators 100, 120 are off. In an embodiment, when the sidewall illuminators 200a-d are on, sidewall illumination output thereby travels to and through corresponding sidewall beam splitters 210a-d, toward the component's sidewalls 26a-d along optical paths that are parallel/substantially parallel to the x axis or the y axis (depending upon which sidewall illuminator 200a-d and sidewall beam splitter 210a-d are under consideration), and perpendicular/substantially perpendicular to the component's sidewalls 26a-d and each corresponding sidewall imaging plane 420a-d.

A portion of the sidewall illumination that passes through the sidewall beam splitters 210a-d will be incident upon the component sidewalls 26a-d, and is reflected thereby back toward the sidewall beam splitters 210a-d. The sidewall beam splitters 210a-d redirect this reflected sidewall illumination toward the image capture beam splitter 110, whereupon it is further redirected toward and into the lens assembly 300 and the image capture device 400 to facilitate the capture of images of component sidewalls 26a-d.

Some of the sidewall illumination emitted by the sidewall illuminators 200a-d that passes through the sidewall beam splitters 210a-d will not be incident upon component sidewalls 26a-d, but will instead travel to an opposite side sidewall beam splitter 210a-d, whereupon it will be redirected toward the image capture beam splitter 110, whereupon it is further redirected toward and into the lens assembly 300 and the image capture device 400. For instance, when the first sidewall beam splitter 210a receives first sidewall illumination provided by the first sidewall illuminator 200a, a portion of the first sidewall illumination transmitted through the first sidewall beam splitter 210a will be incident on the first component sidewall 26a and reflected thereby, while another portion of the first sidewall illumination transmitted through the first sidewall beam splitter 210a not incident on and reflected (or blocked) by the first component sidewall 26a, will travel past the component 20 to the second sidewall beam splitter 210b, which is on the opposite side of the sidewall inspection area 30 from the first sidewall beam splitter 210a. This first sidewall illumination that has not been reflected (or blocked) by the first component sidewall 26a which travels to the second sidewall beam splitter 210b can be received and redirected by the second sidewall beam splitter 210b as extraneous first sidewall illumination. Some of the extraneous first sidewall illumination may illuminate the component sidewall 26b resulting in 'cross talk' in the image of the component sidewall 26b. Similarly, when the second sidewall beam splitter 210b receives second sidewall illumination provided by the second sidewall illuminator 200b, a portion of the second sidewall illumination transmitted through the second sidewall beam splitter 210b will be incident upon and reflected by the second component sidewall 26b, while another portion of the second sidewall illumination transmitted through the second sidewall beam splitter 210b will not be incident on and reflected (or blocked) by the second component sidewall 26b, but will instead travel past the component 20 to the first sidewall beam splitter 210a, which is on the opposite side of the sidewall inspection area 30 from the second sidewall beam splitter 210b. This second sidewall illumination that is not reflected (or blocked) by the second component sidewall 26b can be received and redirected by the first sidewall beam splitter 210a as extraneous second sidewall illumination. Some of these extraneous second sidewall illumination may illuminate the component sidewall 26a resulting in 'cross talk' in the image of the component sidewall 26a. Analogously, when the third sidewall beam splitter 210c receives third sidewall illumination provided by the third sidewall illuminator 200c, a portion of the third sidewall illumination transmitted through the third sidewall beam splitter 210c will be incident on and reflected by the third component sidewall 26c, while another portion of the third sidewall illumination transmitted through the third sidewall beam splitter 210c will not be incident on and reflected by the third component sidewall 26c, but will instead travel past the component 20 to the fourth sidewall beam splitter 210d, which is on the opposite side of the sidewall inspection area 30 from the third sidewall beam splitter 210c. This third sidewall illumination that has not been reflected by the third component sidewall 26c but which instead travels to the fourth sidewall beam splitter 210d can be received and redirected by the fourth sidewall beam splitter 210d as extraneous third sidewall illumination. Correspondingly, when the fourth sidewall beam splitter 210d receives fourth sidewall illumination provided by the fourth sidewall illuminator 200d, a portion of the fourth sidewall illumination transmitted through the fourth sidewall beam splitter 210d will be incident on and reflected by the fourth component sidewall 26d, while another portion of the fourth sidewall illumination transmitted through the fourth sidewall beam splitter 210d will not be reflected by the fourth component sidewall 26d, but will instead travel past the component 20 to the third sidewall beam splitter 210c, which is on the opposite side of the sidewall inspection area 30 from the fourth sidewall beam splitter 210d. This fourth sidewall illumination that has not been reflected by the fourth component sidewall 26d but which instead travels to the third sidewall beam splitter 210c can be received and redirected by the third sidewall beam splitter 210c as extraneous fourth sidewall illumination. Such illumination output by the sidewall illuminators which was not reflected by any component sidewall 26a-d or component structure associated therewith is extraneous sidewall illumination, which is a type of optical crosstalk. In accordance with various embodiments of the present disclosure, the reduction, elimination, or effective elimination of extraneous illumination including extraneous sidewall illumination and corresponding "optical crosstalk" or the effect(s) associated therewith relative to an inspection process performed upon a captured image that includes component sidewalls or sidewall image regions therein results in a significantly or greatly enhanced ability to detect micro-defects in sidewall images, which is not possible when conventional extraneous illumination (e.g., extraneous brightfield illumination and/or extraneous darkfield illumination) is present, or when extraneous sidewall illumination is present, or when no compensation for the presence of extraneous sidewall illumination has occurred/is performed. In multiple embodiments, the reduction, elimination, or effective elimination of extraneous sidewall illumination or the effect(s) thereof on sidewall inspection is achieved by way of (a) selective activation of particular sidewall illuminators 200a-d at particular times such that sidewall illumination of the same or overlapping optical wavelengths or optical bandwidths is prevented from being simultaneously transmitted through opposing sidewall beam splitters 210a,b, 210c,d; and/or (b) the provision or generation of optical wavelength or optical bandwidth segregated sidewall illumination and/or reflected sidewall illumination corresponding to opposing sidewall beam splitters 210a,b, 210c,d, as further detailed below.

Figure 4B:
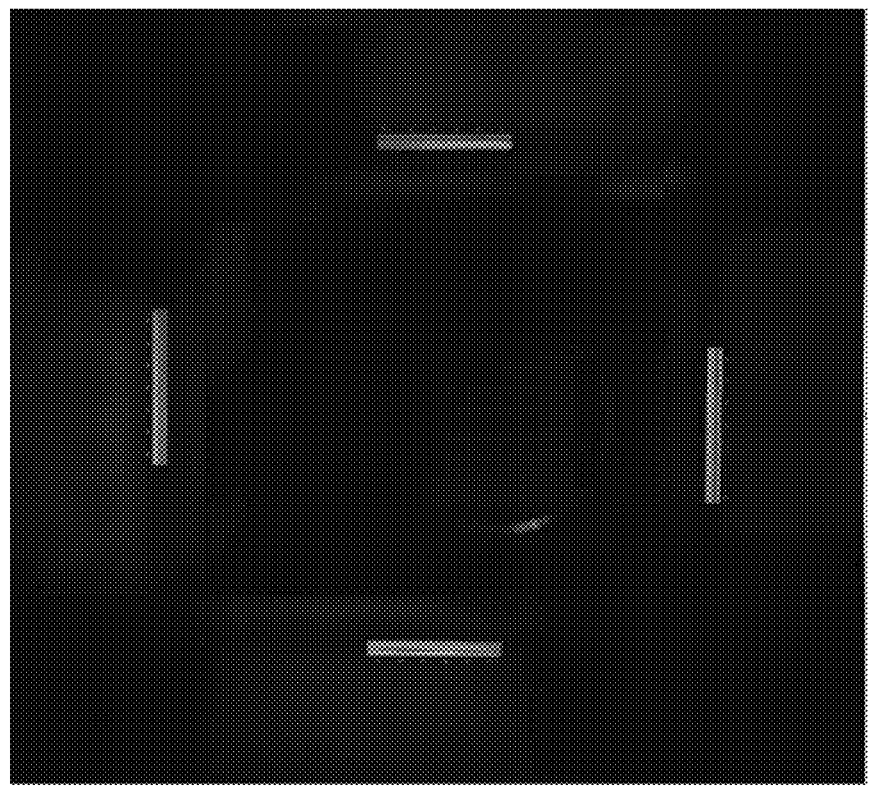
FIG. 4B is a representative multi-sidewall image showing four individual sidewall images therein, which corresponds to sidewall inspection operations that occur when a component is positioned at the sidewall inspection position, a brightfield illuminator is inactive, and sidewall illuminators are active.

FIG. 4B is a representative multi-sidewall image showing four individual sidewall images therein, which corresponds to sidewall inspection operations that occur when the component 20 is positioned at a centered sidewall inspection position within the sidewall inspection area 30, the brightfield illuminator 100 and the darkfield illuminator 120 are inactive or off, and particular sidewall illuminators 200a-d (e.g., one of a pair of opposing pair of sidewall illuminators 210a,b, 210c,d) are active at particular/distinct times, or each sidewall illuminator 200a-d is active (e.g., in an optical wavelength or optical bandwidth segregated manner) simultaneously, as further elaborated upon below.

An individual having ordinary skill in the relevant art will recognize that a multi-sidewall image such as that shown in FIG. 4B can also be generated when (a) opposing sidewall illuminators 200a,b, 200c,d are simultaneously outputting sidewall illumination at an identical or overlapping optical wavelength or wavelength range, and (b) one or more sets of anti-reflective coatings and/or optical polarization techniques and/or polarizing elements/structures (e.g., polarizing filters) are disposed relative to optical paths along which sidewall illumination can be transmitted (i) through a given sidewall beam splitter 210a,c, 210b,d, (ii) across the sidewall inspection area 30, and (iii) to an opposing sidewall beam splitter 210b,c, 210a,c, thereby reducing, minimizing, or effectively eliminating optical crosstalk arising from extraneous sidewall illumination, and/or the effect(s) thereof on sidewall inspection operations. For example, in one embodiment, it may be possible to have each of the wall illuminators 200a-d to emit the same wavelength of light to illuminate the corresponding component sidewalls 26a-d passing through the corresponding sidewall beam splitters 210a-d. However, each of the opposing pairs of sidewall beam splitters (eg 210 b&c) will have to be fitted with polarizers (eg. Wire grid polarizers) set at different polarizing angle so that light of particular polarization passing through one of the sidewall beam splitters 210b (not blocked by the corresponding component sidewall 26a) and crossing over to the opposite sidewall beam splitter 210c would be absorbed or reflected away from the opposite component sidewall 26c) by another polarizer coupled to the said opposite sidewall beam splitter 210c; and vice versa. In this manner, extraneous light (cross talk) from opposing sidewall illumination 200a-d can be eliminated such that only light of particular polarization passing through one of the sidewall beam splitter 210a-d will be reflected off the corresponding component sidewall 26a-d while the extraneous components thereof in absorbed by polarizer at the opposing side wall beam splitters. This method is particular useful if broadband illumination (mixed oscillations) for sidewall illuminators are desired. With particular polarized light being passing from the polarized beam splitters 210a-d to the corresponding component sidewalls, not only is optical cross talk eliminated but a much clearer and sharper image of the ultrafine defect can be captured using a monochrome camera.

Figure 1B:
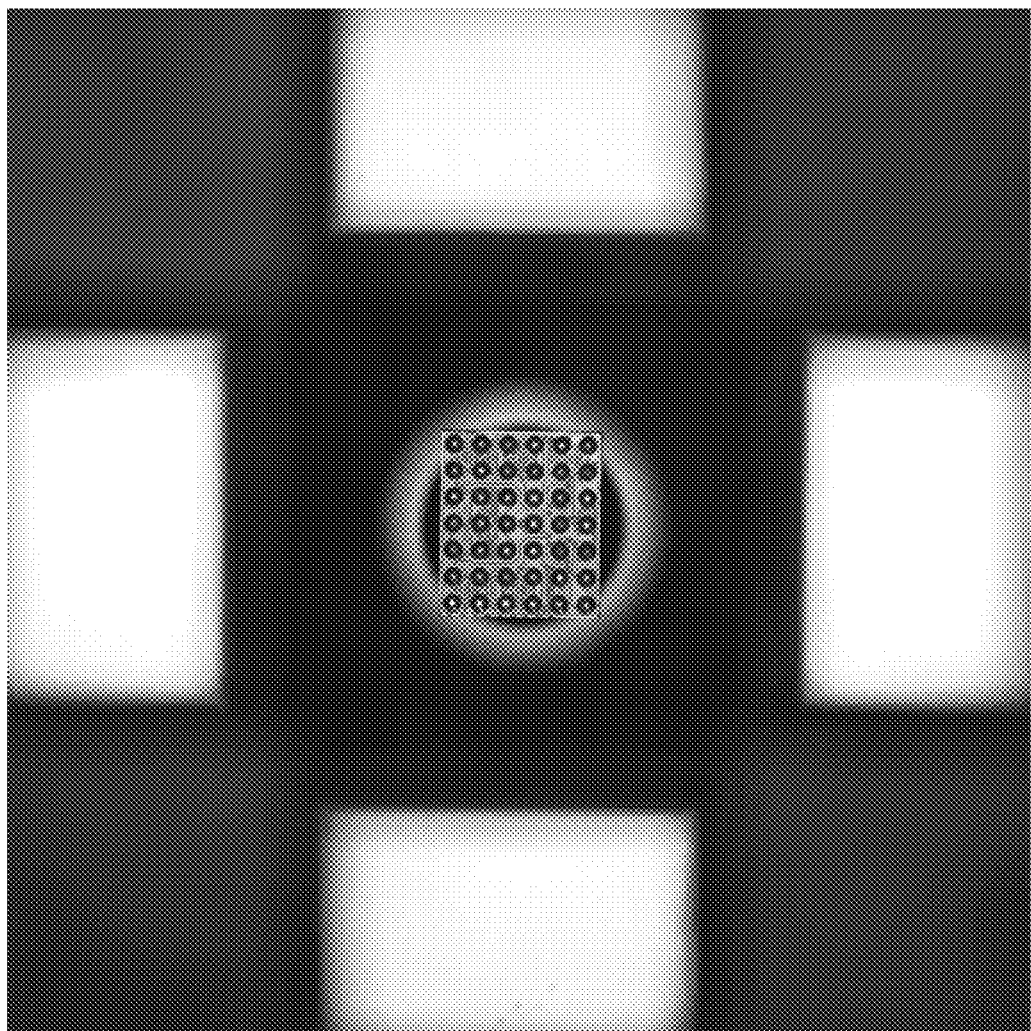
FIG. 1B is a representative inspection image captured while a component is held at a bottom surface inspection position corresponding to the inspection configuration shown in FIG. 1A.
Figure 1C:
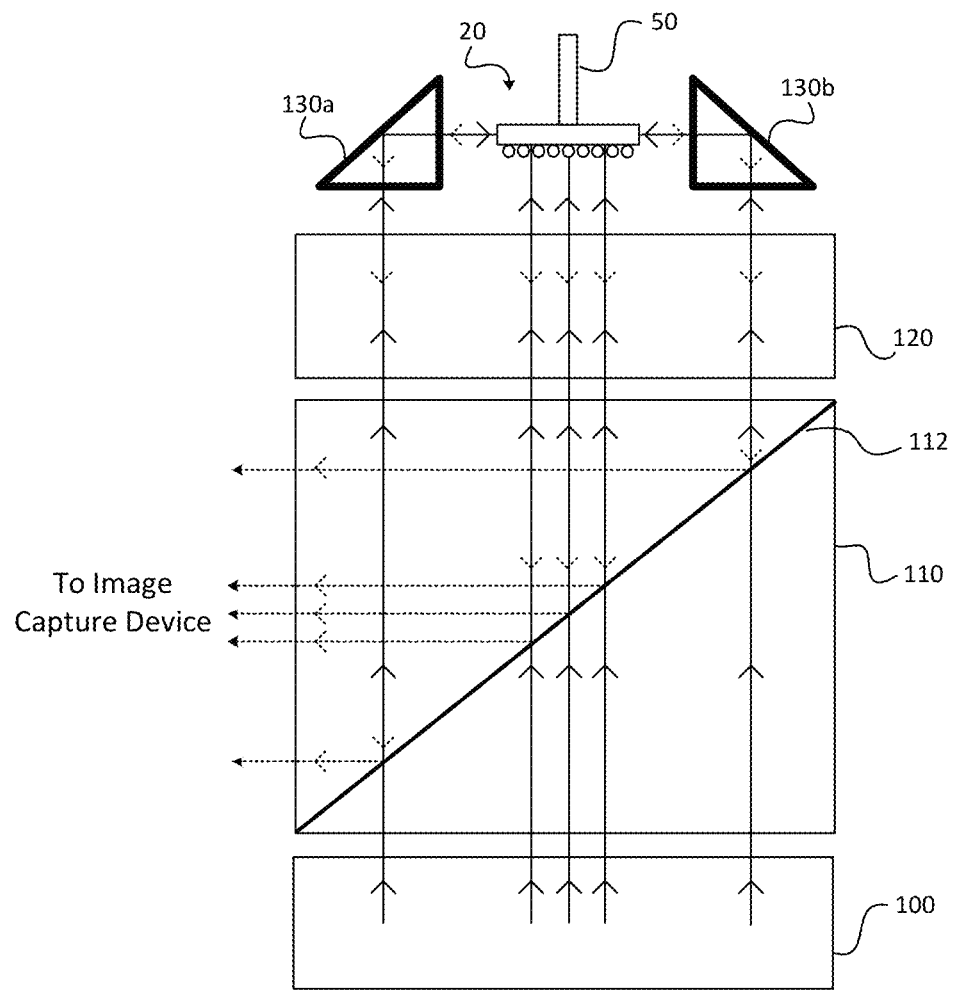
FIG. 1C is a schematic illustration showing portions of the conventional five side inspection apparatus of FIG. 1A, in which the component is held by the component holder at a sidewall inspection position.
Figure 1D:
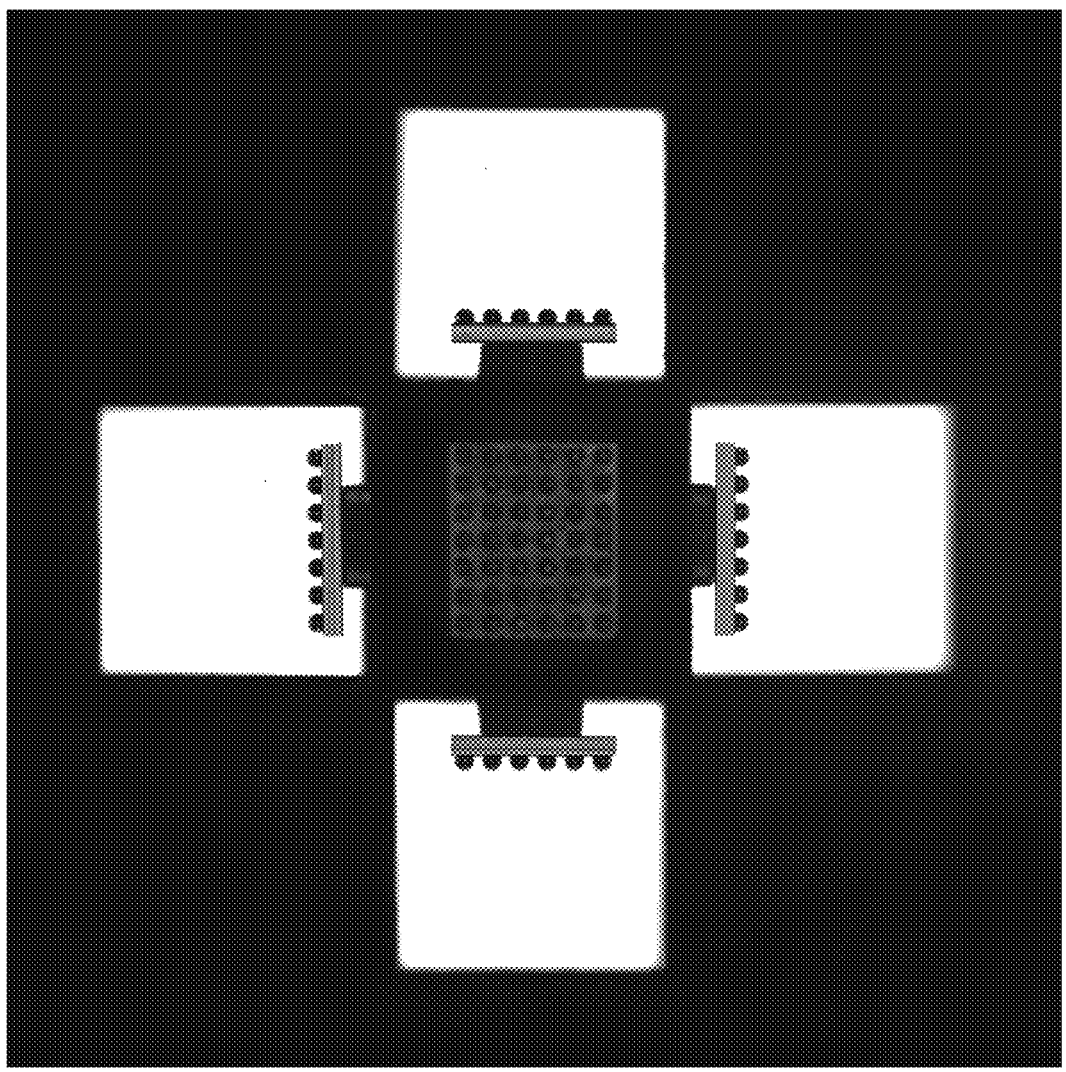
FIG. 1D is a representative inspection image captured while the component is held at the sidewall inspection position.
Figure 1E:
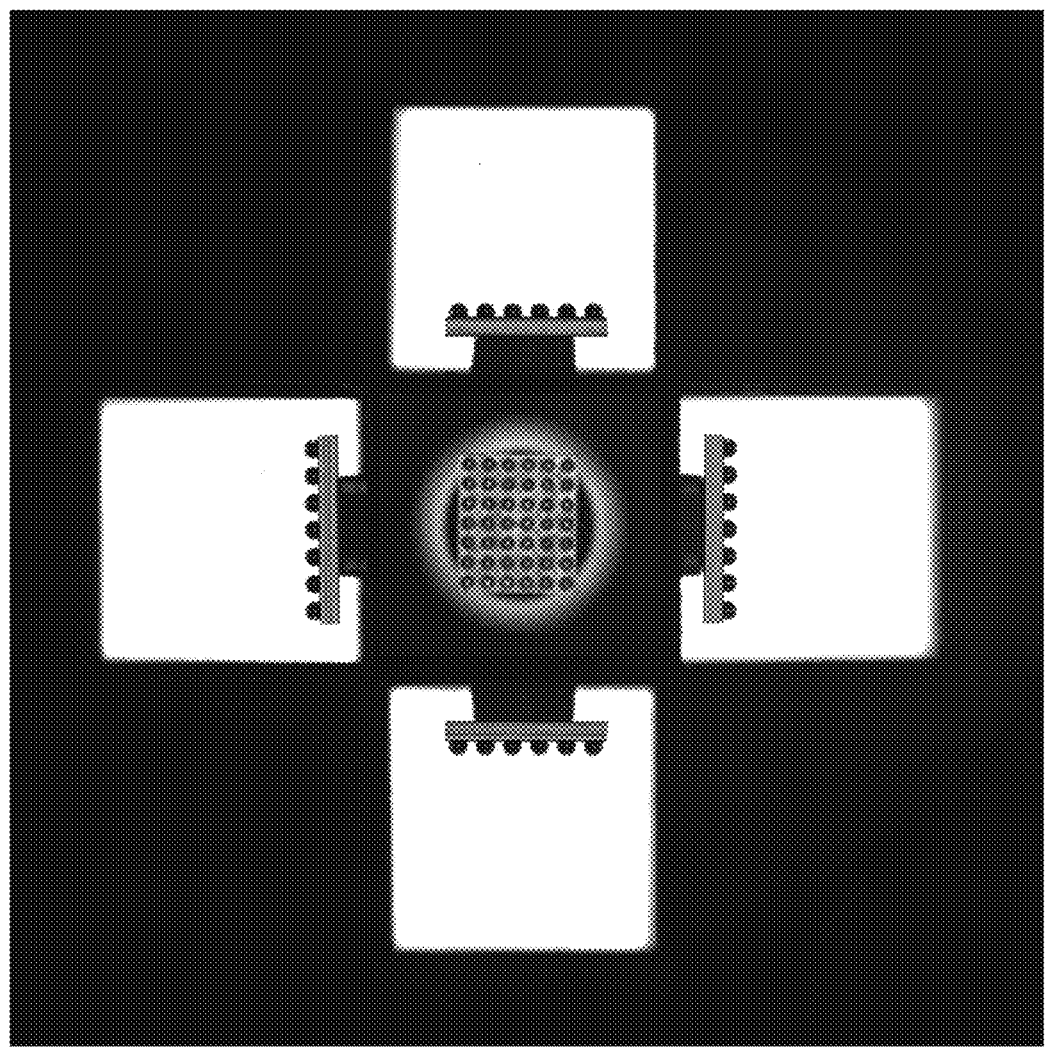
FIG. 1E provides a representative composite image generated by way of combining or digitally stitching together central and peripheral portions of a bottom surface inspection image and a sidewall inspection image, respectively.
Figure 1F:
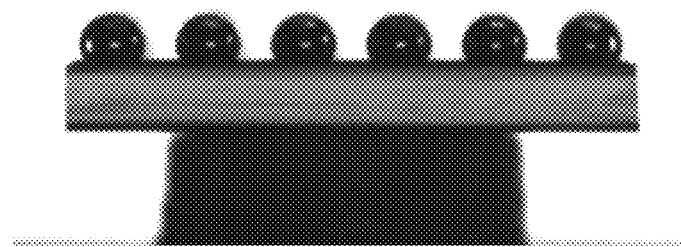
FIG. 1F illustrates a portion of the composite image corresponding to a component sidewall.
Figure 4C:
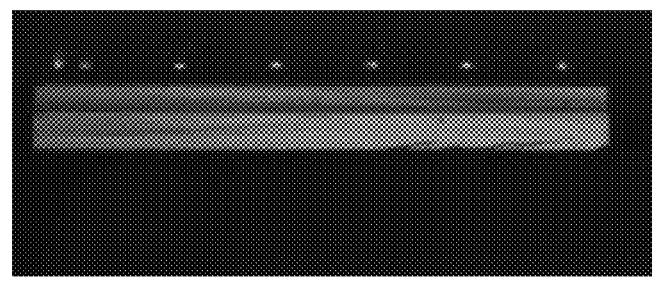
FIG. 4C is a representative individual sidewall image obtained from FIG. 4B.

FIG. 4C is a representative individual sidewall image obtained from FIG. 4B. A comparison between FIG. 4B and FIG. 1F clearly indicates that fine, ultrafine, or micro-scale features in the sidewall image corresponding to actual sidewall structural features, shadows, and/or defects are much more clearly defined in FIG. 4B than FIG. 1B. Hence, embodiments in accordance with the present disclosure can greatly enhance the detection of fine, ultrafine, or micro-scale defects (less than or equal to approximately 5 µm) in captured sidewall images, and correspondingly greatly enhances image processing based sidewall inspection accuracy.

In some embodiments, a multi-sidewall image such as that shown in FIG. 4B can be captured as a single view in a single image capture operation by way of deactivating/turning off the brightfield illuminator 100 while each of the sidewall illuminators 200a-d is turned on simultaneously in an appropriate optical wavelength or optical bandwidth segregated manner when the component 20 is positioned at or generally at the centered sidewall inspection position and an image captured, as further detailed below. Alternatively, such a multi-sidewall image can be generated as a composite image from multiple captured images that are generated by way of distinct or separate image capture operations when the component 20 resides at the centered sidewall inspection position. Each image from which the composite image is generated corresponds to a particular subset of activated sidewall illuminators 200a-d that was activated at a particular time during a given image capture operation, and thus each such image from which the composite image is generated includes image data (e.g., pixel values) associated with a particular corresponding subset of component sidewalls 26a-d. For instance, individual sidewall images corresponding to each component sidewall 26a-d (or each component sidewall 26a-d of interest) can be captured individually/separately/sequentially using sidewall illuminators 200a-d configured for outputting sidewall illumination of identical or overlapping optical wavelengths or optical bandwidths. Alternatively, multiple sidewall images corresponding to non-opposing pairs of component sidewalls 26a,c-26b,d/26a,d-26b,c, which exclude sidewall images of opposing component sidewalls 26a,b, 26c,d, can be separately/sequentially/successively captured using (a) incident sidewall illumination having the same optical wavelength or optical bandwidth (in association with an image capture device 400 having a monochrome or color image sensor), or (b) incident sidewall illumination of different optical wavelengths or optical bandwidths (in association with an image capture device 400 having a color image sensor), as described in greater detail hereafter.

Representative Selective Activation of Sidewall Illuminators

In several embodiments, sidewall illuminators 200a-d can be turned on or activated individually or in particular subsets (e.g., pairwise, in a manner that avoids simultaneous transmission of sidewall illumination through opposing sidewall beam splitters 210a,b, 210c,d) in a manner that further reduces, eliminates, or effectively eliminates extraneous sidewall illumination in captured sidewall images or the effect(s) thereof on sidewall inspection based upon captured sidewall images, thereby further enhancing sidewall inspection accuracy. Such selective activation of sidewall illuminators 200a-d can involve the selective transmission of monochrome or essentially monochrome sidewall illumination or color sidewall illumination through specific sidewall beam splitters 210a-d and onto corresponding specific component sidewalls 26a-d. An individual having ordinary skill in the relevant art will understand that monochrome illumination can be captured by way of a monochrome image sensor or a color image sensor; and color illumination can be captured by way of a color image sensor such that different optical wavelengths corresponding to different color pixel data values or color pixel value ranges within image data corresponding to a captured image can be readily distinguished and/or separately processed to facilitate sidewall inspection operations.

Figure 5A:
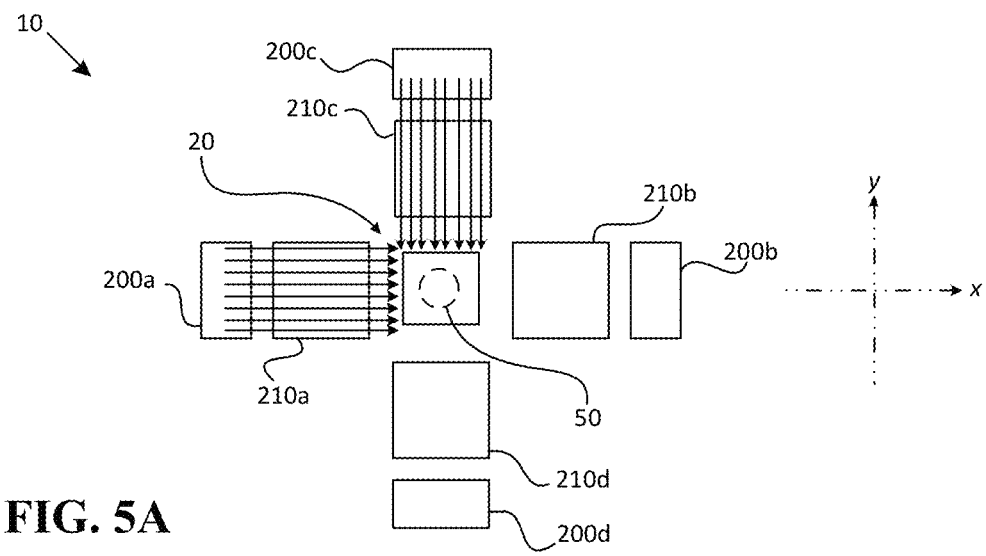
FIG. 5A is a schematic illustration of a representative first sidewall illuminator activation pattern in accordance with an embodiment of the present disclosure.

For instance, FIG. 5A is a schematic illustration of a representative first sidewall illuminator activation pattern in which a first sidewall illuminator 200a and an adjacent third sidewall illuminator 200c are activated or on; and a second sidewall illuminator 200b opposite to the first sidewall illuminator 200a and a fourth sidewall illuminator 200d opposite to the third sidewall illuminator 200c remain inactive or off. As a result of such a sidewall illuminator activation pattern, a captured sidewall image corresponding to the first component sidewall 26a will not include or be affected by extraneous sidewall illumination associated with the second sidewall illuminator 200b; and a captured sidewall image corresponding to the third component sidewall 26*c* will not include or be affected by extraneous sidewall illumination associated with the fourth sidewall illuminator 200*d*.

When oppositely disposed sidewall illuminator pairs 200*a-b*, 200*c-d* are activated such that only one sidewall illuminator 200*a-b*, 200*c-d* within each pair of oppositely disposed sidewall illuminators 200*a-b*, 200*c-d* outputs illumination during a given image capture operation, extraneous sidewall illumination that would otherwise be associated with the currently inactive sidewall illuminator 200*a-b*, 200*c-d* will not be produced, and hence will not be captured as part of a sidewall image. This can further significantly enhance the clarity of component sidewall features, shadows, and/or defects, and further increase component sidewall inspection accuracy.

Figure 5B:
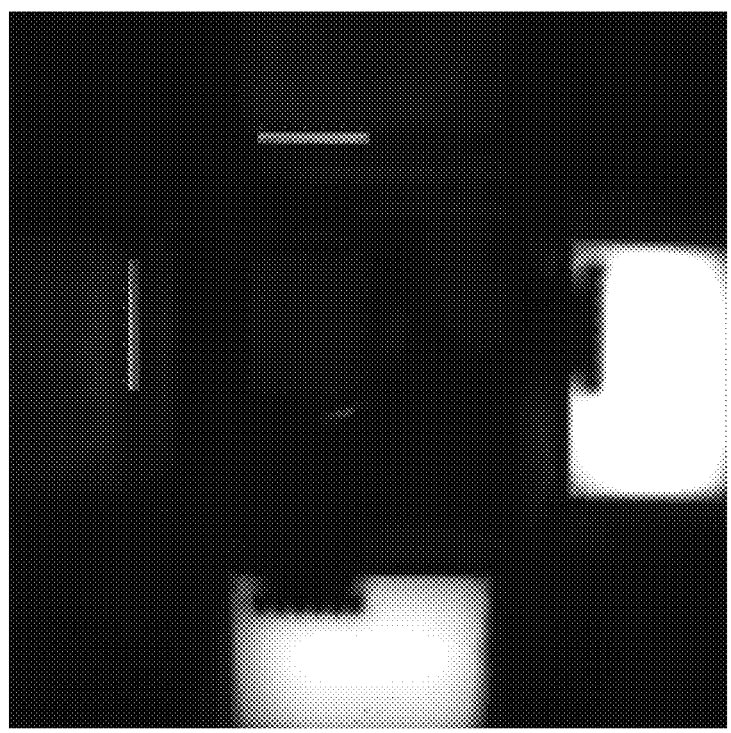
FIG. 5B is a representative first multi-sidewall image captured when a component is positioned at a sidewall inspection position, a first and a third sidewall illuminator are active, and a second and a fourth sidewall illuminators are inactive, corresponding to the first sidewall illuminator activation pattern of FIG. 5A.

FIG. 5B is a representative first multi-sidewall image captured when the component 20 is positioned at the centered sidewall inspection position, the first and third sidewall illuminators 200*a,c* are active, and the second and fourth sidewall illuminators 200*b,c* are inactive, corresponding to the first sidewall illuminator activation pattern of FIG. 5A. As indicated in FIG. 5B, this first multi-sidewall image includes a left image region in which pixels clearly represent or contain useful information corresponding to the first component sidewall 26*a*; and an upper image region in which pixels clearly represent or contain useful information corresponding to the third component sidewall 26*c*. The first multi-sidewall image does not include image regions having pixels that clearly represent or contain useful information corresponding to the second or fourth sidewalls 26*b,d*, because the corresponding sidewall illuminators 200*b,d* were off during image capture operations. That is, since the first and third sidewall illuminators 200*a,c* were active during image capture operations, and the second and fourth sidewall illuminators 200*b,d* were inactive during image capture operations, the resulting captured image includes detailed sidewall images or sidewall image regions corresponding to the first and third component sidewalls 26*a,c*, but excludes detailed sidewall images or sidewall image regions corresponding to the second and fourth component sidewalls 26*b,d*.

Figure 5C:
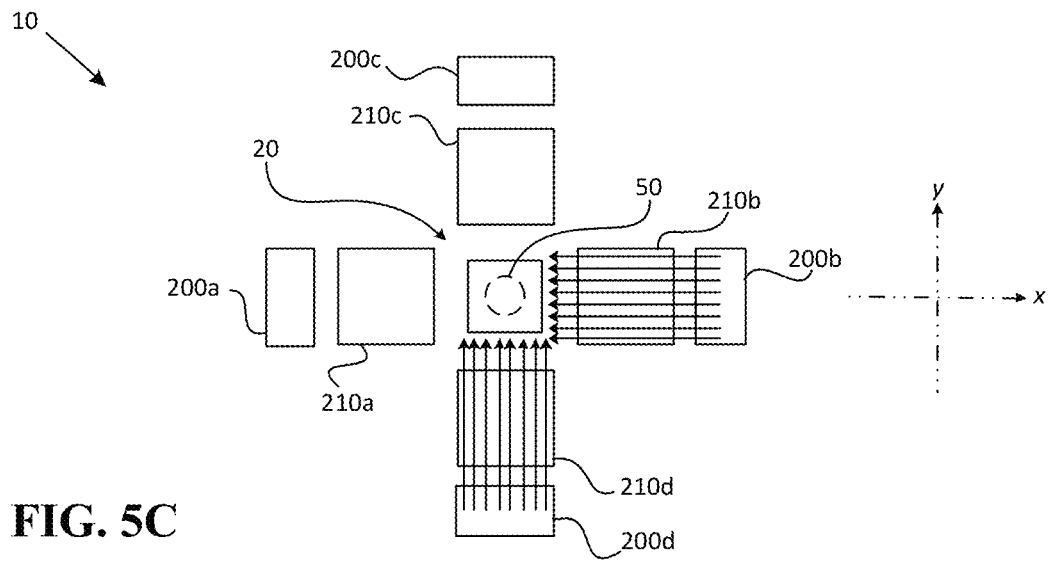
FIG. 5C is a schematic illustration of a representative second sidewall illuminator activation pattern in accordance with an embodiment of the present disclosure.

Similarly, FIG. 5C illustrates a representative second sidewall illuminator activation pattern in which the second sidewall illuminator 200*b* and its adjacent fourth sidewall illuminator 200*d* are activated or on; and the first sidewall illuminator 200*a* and the third sidewall illuminator 200*c* remain inactive or off. As a result, a captured sidewall image corresponding to the second component sidewall 26*b* will not include or be affected by extraneous sidewall illumination associated with the first sidewall illuminator 200*a*; and a captured sidewall image corresponding to the fourth component sidewall 26*d* will not include or be affected by extraneous sidewall illumination associated with the third sidewall illuminator 200*c*.

Figure 5D:
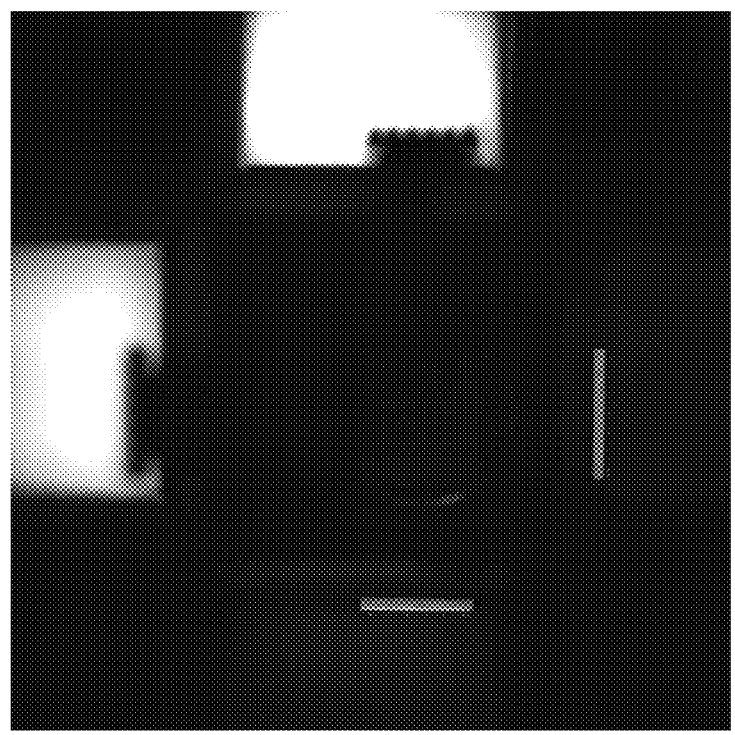
FIG. 5D is a representative second multi-sidewall image captured when a component is positioned at the sidewall inspection position, the second and the fourth sidewall illuminators are active, and the first and third sidewall illuminators are inactive, corresponding to the second sidewall illuminator activation pattern of FIG. 5C.

FIG. 5D is a representative second multi-sidewall image captured when the component 20 is positioned at the centered sidewall inspection position, the second and fourth sidewall illuminators 200*b,d* are active, and the first and third sidewall illuminators 200*a,c* are inactive, corresponding to the second sidewall illuminator activation pattern of FIG. 5C. As indicated in FIG. 5D, this second multi-sidewall image includes a right image region in which pixels clearly represent or contain useful information corresponding to the second component sidewall 26*b*; and a lower image region in which pixels clearly represent or contain useful information corresponding to the fourth component sidewall 26*d*. The second multi-sidewall image does not include image regions having pixels that clearly represent or contain useful information corresponding to the first or third sidewalls 26*a,c*, because the corresponding sidewall illuminators 200*a,c* were off during image capture operations. That is, since the second and fourth sidewall illuminators 200*b,d* were active during image capture operations, and the first and third sidewall illuminators 200*a,c* were inactive during image capture operations, the resulting captured image includes detailed sidewall images or sidewall image regions corresponding to the second and fourth component sidewalls 26*b,d*, but excludes detailed sidewall images or sidewall image regions corresponding to the first and third component sidewalls 26*a,c*.

For purpose of sidewall inspection (e.g., automated sidewall defect inspection), some embodiments perform separate image processing operations on (a) individual sidewall images, or (b) multi-sidewall images that include image regions having pixels that clearly represent or contain useful information corresponding only to specific subsets of component sidewalls 26*a-d* (e.g., automated sidewall defect inspection can be performed on two separate multi-sidewall images, each of which includes image regions having pixels that clearly represent or contain useful information corresponding to a particular adjacent pair of component sidewalls 26*a,c*-26*b,d*/26*a,d*-26*b,c*). However, particular embodiments can additionally or alternatively generate a single composite multi-sidewall image that includes image regions having pixels that clearly represent or contain useful information corresponding to each component sidewall 26*a-d* (or each component sidewall 26*a-d* of interest within a plurality of component sidewalls 26*a-d*, which can include opposing component sidewalls 26*a,b*, 26*c,d*), and perform image processing operations upon the single composite image.

Figure 5E:
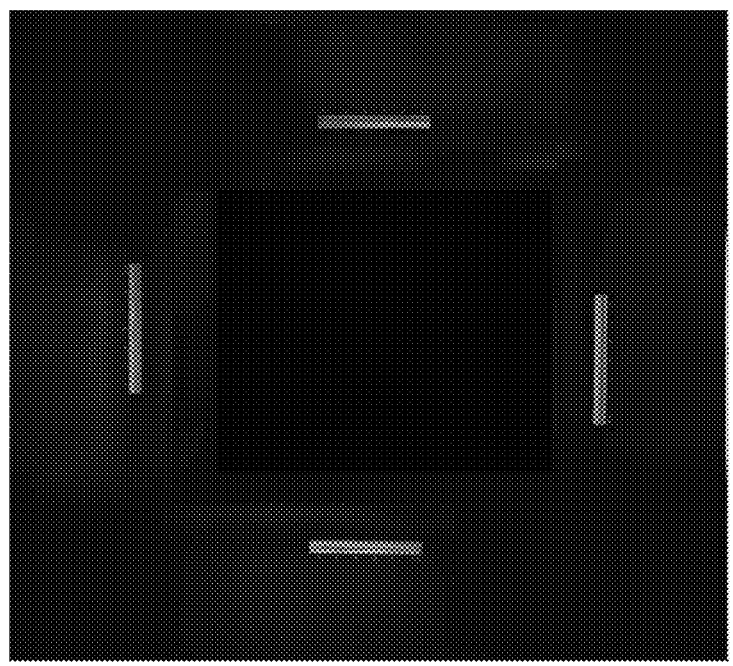
FIG. 5E is a representative composite multi-sidewall image generated from the first multi-sidewall image of FIG. 5B and the second multi-sidewall image of FIG. 5D.

A representative single composite multi-sidewall image can be generated by way of digitally stitching together those portions of the aforementioned first multi-sidewall image that contain detailed sidewall images or sidewall image regions corresponding to a first subset of component sidewalls 26*a-d*, and those portions of the aforementioned second multi-sidewall image that contain detailed sidewall image or image regions corresponding to a second subset of component sidewalls 26*a-d*, while excluding form the composite image portions of each of the first and second multi-sidewall images that do not contain detailed sidewall images or sidewall image regions. More particularly, a single composite multi-sidewall image can be generated from the first and second multi-sidewall images by digitally combining or stitching together the left image region of the first multi-sidewall image, the upper image region of the first multi-sidewall image, the right image region of the second multi-sidewall image, and the lower image region of the second multi-sidewall image. In some embodiments, a central region of the composite multi-sidewall image can be filled with predetermined pixel values (e.g., corresponding to a black color) if desired or required. FIG. 5E is a representative composite multi-sidewall image generated from the first multi-sidewall image of FIG. 5B and the second multi-sidewall image of FIG. 5D.

As previously indicated, in addition to the foregoing, in several embodiments the component holder 50 can selectably/selectively position a component 20 carried thereby at one or more lateral or x-y plane positions other than the centered sidewall inspection position within the sidewall inspection area 30, such the component 20 is closer to certain sidewall beam splitters 210*a-d* than other sidewall beam splitter 210a-d. Thus, the component holder 50 can selectably/selectively/programmably/intentionally position the component 20 "off center" between two or more sidewall beam splitters 210a-d, such that the component 20 is disposed towards a particular edge, side, or corner within the sidewall inspection area 30, and is therefore disposed or biased toward a particular edge, side, or corner corresponding to or formed by certain sidewall beam splitters 210a-d, and away from another edge, side, or corner corresponding to or formed by one or more other sidewall beam splitters 210a-d. For instance, the component holder 50 can position the component 20 such that a centroid or center point of the component (e.g., defined as a center point within the body of the component 20, or a center point on the component's bottom and/or top surface 22, 24) is disposed toward or closer to a particular (e.g., first) subset of sidewall beam splitters 210a,c that share a first corresponding or common boundary or border (e.g., as a result of their adjacency) than another (e.g., second) subset of sidewall beam splitters 210b,d that share a second corresponding or common boundary or border (e.g., as a result of their adjacency).

Figures 5F, 5G:
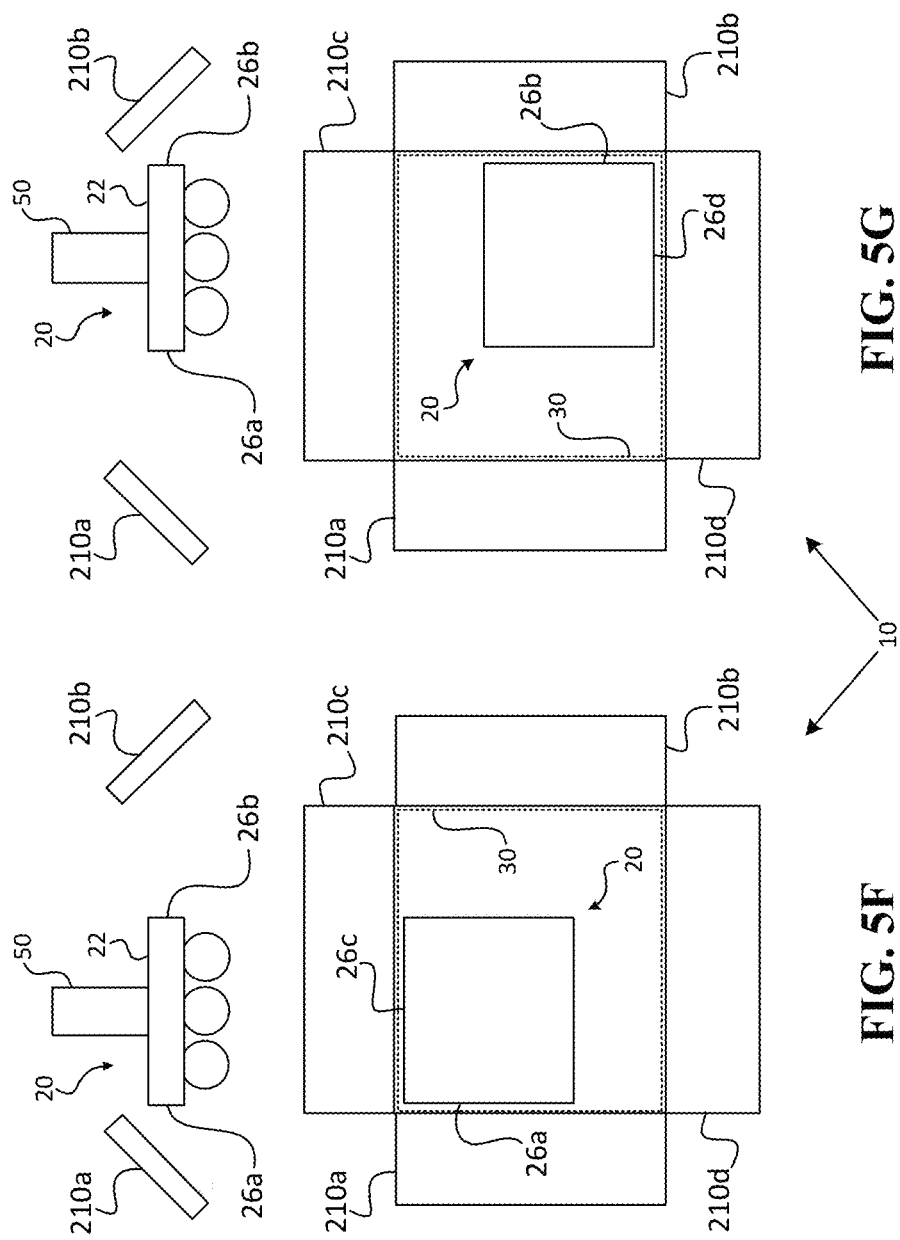
FIG. 5F illustrates a schematic top and side view of a component disposed at a representative first off-center sidewall inspection position within a sidewall inspection area in accordance with an embodiment of the present disclosure.
FIG. 5G illustrates a schematic top and side view of the component of FIG. 5F disposed at a representative second off-center sidewall inspection position within the sidewall inspection area in accordance with an embodiment of the present disclosure.

FIG. 5F illustrates a schematic top and side view of a component 20 disposed at a representative first off-center sidewall inspection position within the sidewall inspection area 30, such that a component center point 21 is closer to a first subset of non-opposing sidewall beam splitters 210a-d, such as a first and a third sidewall beam splitter 210a,c than a second subset of non-opposing sidewall beam splitters 210a-d, such as a second and a fourth sidewall beam splitter 210b,d. Similarly, FIG. 5G illustrates a schematic top and side view of the component 20 disposed at a representative second off-center sidewall inspection position within the sidewall inspection area 30, such that the component center point 21 is closer to the second and fourth sidewall beam splitters 210b,d than the first and third sidewall beam splitters 210a,c.

While the component is disposed at the first off-center sidewall inspection position, (a) the first and third sidewall illuminators 200a,c can be activated while the second and fourth sidewall illuminators 200b,d remain inactive. Consequently, illumination output by the first and third sidewall illuminators 200a,c is respectively transmitted through the first and third sidewall beam splitters 210a-c, and is incident upon the first component sidewall 26a and the third component sidewall 26c, whereupon it is reflected thereby/therefrom as reflected sidewall illumination. Reflected sidewall illumination traveling away from the first and third component sidewalls 26a,c is redirected by the first and third sidewall beam splitters 210a,c, respectively, toward and to the image capture beam splitter 100, whereupon it is further redirected toward the image capture device 400 and captured thereby as a first off-center image (e.g., a first off-center multi-sidewall image).

Because the second and fourth sidewall illuminators 200b,d remain inactive while the component 20 is disposed at the first off-center sidewall inspection position, no sidewall illumination from the second and fourth sidewall illuminators 200b,d is incident on the component 20 (e.g., on the second and fourth component sidewalls 26b,d, respectively) during the capture of the first off-center image. Furthermore, because the second sidewall beam splitter 210b and the fourth sidewall beam splitter 210d are positioned opposite to the first sidewall beam splitter 210a and the third sidewall beam splitter 210c, respectively, the reflection of illumination by the second and fourth component sidewalls 26b,d during the capture of the first off-center image is greatly reduced, minimized, or essentially eliminated. Hence, during the capture of the first off-center image, extraneous sidewall illumination or optical crosstalk associated with the second and fourth sidewall beam splitters 210b,d is greatly reduced, minimized, or essentially eliminated.

After the capture of the first off-center image, the component 20 can be moved relative to the set of sidewall beam splitters 26a-d such that the component resides at the second off-center sidewall inspection position. While the component is disposed at the second off-center sidewall inspection position, (a) the second and fourth sidewall illuminators 200b,d can be activated while the first and third sidewall illuminators 200a,c remain inactive. Consequently, illumination output by the second and fourth sidewall illuminators 200b,d is respectively transmitted through the second and fourth sidewall beam splitters 210a-c, and is incident upon the second component sidewall 26b and the fourth component sidewall 26d, whereupon it is reflected thereby/therefrom as reflected sidewall illumination. Reflected sidewall illumination traveling away from the second and fourth component sidewalls 26b,d is redirected by the second and fourth sidewall beam splitters 210b,d, respectively, toward and to the image capture beam splitter 100, whereupon it is further redirected toward the image capture device 400 and captured thereby as a second off-center image (e.g., a second off-center multi-sidewall image).

In a manner analogous to that described above, because the first and third sidewall illuminators 200a,c remain inactive while the component 20 is disposed at the second off-center sidewall inspection position, no sidewall illumination from the first and third sidewall illuminators 200a,c is incident on the component 20 (e.g., on the first and third component sidewalls 26a,c, respectively) during the capture of the second off-center image. Furthermore, because the first and third sidewall beam splitters 210a,c are positioned opposite to the second and fourth sidewall beam splitters 210b,d, respectively, the reflection of illumination by the first and third component sidewalls 26a,c during the capture of the second off-center image is greatly reduced, minimized, or essentially eliminated. Hence, during the capture of the second off-center image, extraneous sidewall illumination or optical crosstalk associated with the first and third sidewall beam splitters 210a,c is greatly reduced, minimized, or essentially eliminated.

The ability to position components 20 at multiple locations within the sidewall inspection area 30 enables an apparatus 10 in accordance with an embodiment of the present disclosure to successfully inspect components 20 of a wide(r) range of sizes with a single arrangement of sidewall beam splitters 210a-d. As a representative example, square, approximately square, or rectangular components 20 having dimensions between approximately 0.3 cm-3.0 cm or larger (e.g., up to approximately 7.0 cm or more, depending on embodiment details and/or component inspection requirements) on each side can undergo sidewall inspection in a manner set forth herein using a single set of sidewall beam splitters 210a-d spaced apart from each other to provide an overall sidewall inspection area of approximately 3.5 cm×3.5 cm. As a result, an owner or user of an apparatus 10 in accordance with an embodiment of the present disclosure need not obtain or purchase a large number of separate optical assemblies, where each optical assembly includes a set of sidewall beam splitters 210a-d configured to provide an inspection area 30 capable of accommodating components 20 of a specific size or planar area (e.g., defined relative to the x-y plane), or a very limited range of sizes/planar areas. Consequently, the cost of ownership of the apparatus 10 is significantly or greatly reduced compared to conventional inspection apparatus designs. More particularly, in conventional inspection apparatus 10 designs, a given optical assembly (e.g., of the type described above with respect to FIGS. 1A-1F) can be used only for inspecting components 20 having a narrow or very limited range of planar areas (e.g., components 20 of a single planar dimension, or a very small range of planar dimensions). In contrast, an apparatus 10 in accordance with an embodiment of the present disclosure which provides for component positioning 20 at multiple locations within the sidewall inspection area 30 can accommodate components 20 having a much wider range of planar dimensions using a single or the same optical assembly.

Representative Wavelength Segregated Sidewall Illumination and Inspection

In several embodiments, the apparatus 10 is configured such that (a) sidewall illumination traveling toward different or opposite sidewalls 26a-d of a component 20, and/or (b) reflected sidewall illumination traveling away from different or opposite sidewalls 26a-d of the component 20, exhibits a distinct optical center wavelength or wavelength range/bandwidth for each of such different or opposite component sidewalls 20a-d, respectively. As a result, reflected sidewall illumination associated with different or opposite component sidewalls 26 that travels to the image capture device 400 exhibits multiple separate/segregated center wavelengths or wavelength ranges in a manner that corresponds to the particular sidewalls 26a-d from which such reflected sidewall illumination originated. Depending upon embodiment details, center wavelength or wavelength range segregation can occur by way of sidewall illuminators 200a-d configured to output sidewall illumination having different optical center wavelengths or wavelength ranges; and/or optical filters (e.g., separate filter elements, or optical coatings), as further elaborated upon below. In such embodiments, the image capture device 400 is a color camera (e.g., the image capture device 400 includes a color image sensor, in a manner readily understood by an individual having ordinary skill in the relevant art), which enables (a) the simultaneous capture of reflected sidewall illumination corresponding to each component sidewall 26a-d in a single view during a single image capture operation, which results in the generation of a single image in which sidewall image data (e.g., pixel data) clearly represents or contains useful information corresponding to each component sidewall 26a-d; and (b) subsequent optical wavelength/bandwidth based discrimination between or compensation for image data corresponding to each sidewall 26a-d by way of image processing operations as part of automated component sidewall inspection operations.

In some embodiments, each sidewall illuminator 200a-d is configured to output illumination having a distinct optical center wavelength or wavelength range relative to each other sidewall illuminator 200a-d. Because the image capture device 400 includes a color image sensor, each sidewall illuminator 200a-d can be simultaneously active during an image capture operation when a component 20 is disposed at the centered sidewall inspection position. A single image capture operation can thus generate a single set of image data (e.g., pixel data) that clearly represents or contains useful information corresponding to each component sidewall 26a-d. Optical wavelength or bandwidth based digital discrimination or compensation operations can be performed upon the single set of image data as needed to reduce or essentially or effectively eliminate "optical crosstalk" associated with light of different wavelengths from each of the sidewall illuminators 200a,b,c,d that is transmitted through a corresponding sidewall beam splitter 210a,b,c,d and which is not incident upon and therefore not reflected by the corresponding component sidewall 26a-d, but which instead travels past or across the component 20 to an opposing sidewall beam splitter 210 b,a,d,c and is received thereby as extraneous sidewall illumination, and which is redirected as a result of beam splitting such that the extraneous sidewall illumination travels to the color image sensor, as further described hereafter.

Figure 6A:
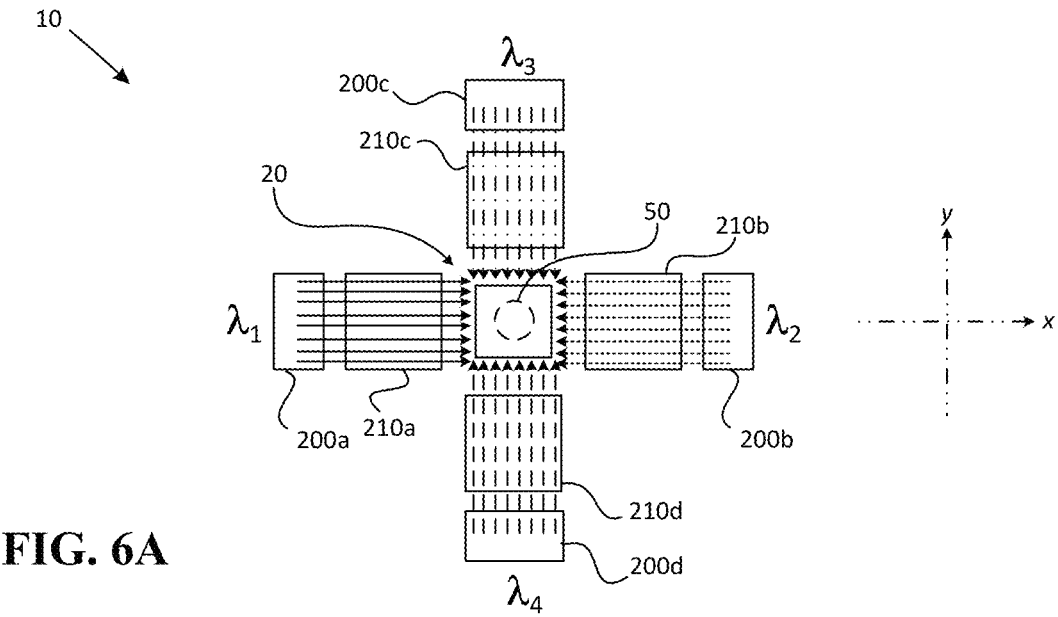
FIG. 6A is a schematic top view illustrating portions of a wavelength segregated sidewall inspection apparatus configured for performing a wavelength segregated sidewall inspection technique in accordance with an embodiment of the present disclosure.

FIG. 6A is a schematic top view illustrating portions of an optical wavelength or bandwidth segregated sidewall inspection apparatus 10 configured for performing an optical wavelength or bandwidth segregated sidewall inspection process or technique in accordance with an embodiment of the present disclosure. In an embodiment, sidewall illumination traveling through each sidewall beam splitter 210a-d toward a given component sidewall 26a-d is bandwidth limited light having a distinct optical center frequency or wavelength relative to sidewall illumination traveling through each other sidewall beam splitter 210a-d toward each other corresponding component sidewall 26a-d. For instance, in a representative implementation, the first sidewall illuminator 200a can output bandwidth limited (e.g., generally narrow, narrow or very narrow bandwidth) light centered at a red wavelength $\lambda_1$ (e.g., approximately 700 nm); the second sidewall illuminator 200b can output bandwidth limited (e.g., generally narrow, narrow, or very narrow bandwidth) light centered at a green wavelength $\lambda_2$ (e.g., approximately 550 nm); the third sidewall illuminator 200c can output bandwidth limited (e.g., generally narrow, narrow, or very narrow bandwidth) light centered at an orange wavelength $\lambda_3$ (e.g., approximately 600 nm); and the fourth sidewall illuminator 200d can output bandwidth limited (e.g., generally narrow, narrow, or very narrow bandwidth) light centered at a blue wavelength $\lambda_4$ (e.g., approximately 450 nm). In various embodiments, the bandwidth of each such center wavelength can be approximately 30 nm (or less) around/about the center wavelength. Such sidewall illumination can be provided by way of LEDs having an appropriate wavelength output, and/or wavelength filters applied to broad spectrum illumination (e.g., white or substantially white light) produced by the sidewall illuminators 200a-d. As further described below with reference to FIG. 6K, to simplify image data generation/collection and processing, in some embodiments adjacent sidewall illuminators 200a,c-200b,d/210a,d-210b,c can be pairwise activated such that (a) one pair of adjacent sidewall illuminators 200a,c-200b,d/200a,d-200b,c can illuminate using light of optical center wavelength $\lambda_1$, while (b) another or counterpart pair of adjacent sidewall illuminators 200a,d-200b,c/200a,c-200b,c can simultaneously illuminate using light of a different optical center wavelength $\lambda_2$, and (c) in any given pair of opposing sidewall illuminators 200a,b, 200c,d under consideration, the opposing sidewall illuminators 200a,b, 200c,d can avoid illuminating using light of the same optical center wavelength $\lambda_1$ or $\lambda_2$. Regardless of whether the embodiment of FIG. 6A or the embodiment of FIG. 6K is considered, as a result of appropriate optical wavelength or optical bandwidth segregation, the optical crosstalk arising from the capture of reflected sidewall illumination by any particular sidewall beam splitter 210a,b,c,d simultaneous with the capture of extraneous sidewall illumination that has been transmitted through its opposing sidewall beam splitter 210b,a,d,c and has traveled across the sidewall inspection area 30 to this particular sidewall beam splitter 210a,b,c,d, thereby "contaminating" the sidewall image corresponding to this particular sidewall beam splitter 210a,b,c,d, can be reduced or eliminated by deducting pixel values falling within a pixel value range corresponding to the optical wavelength or optical bandwidth of the extraneous sidewall illumination from the sidewall image data corresponding to the reflected sidewall illumination that had been captured by the particular sidewall beam splitter 210a,b,c,d under consideration.

Figure 6B:
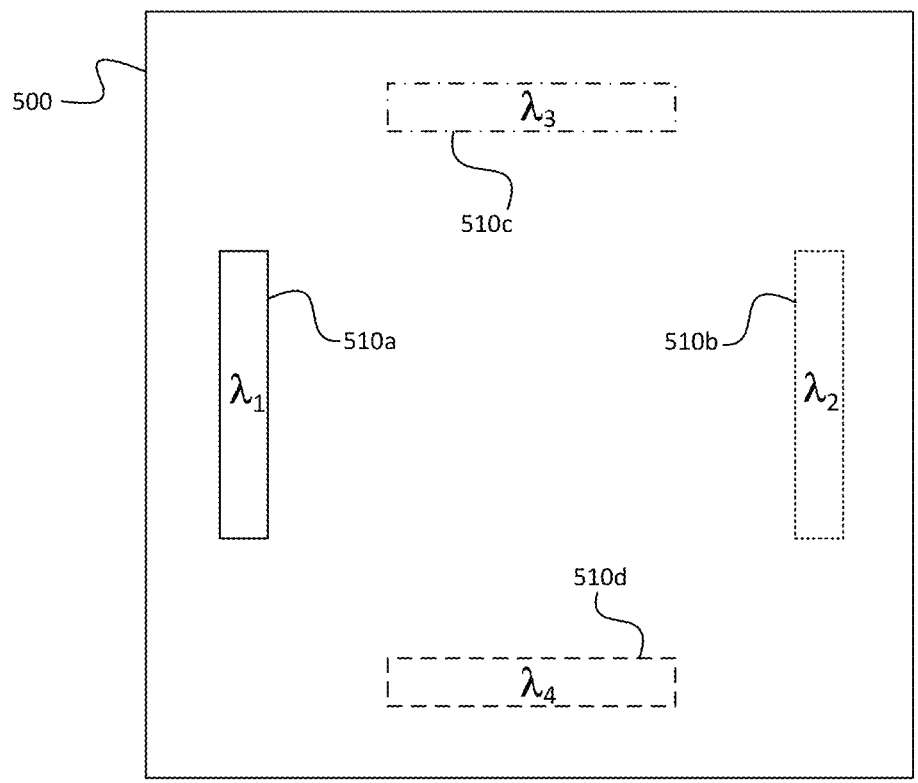
FIG. 6B is a schematic illustration of a representative wavelength segregated multi-sidewall image, which contains four individual sidewall images captured simultaneously using four distinct optical wavelengths/bandwidths, in accordance with an embodiment of the present disclosure.

FIG. 6B schematically illustrates a representative wavelength segregated multi-sidewall image 500 captured as a single view (e.g., in a single image capture operation) by the image capture device 400 by way of the wavelength segregated sidewall inspection apparatus 10 of FIG. 6A. Within such a wavelength segregated multi-sidewall image 500, a first or left sidewall image or sidewall image region 510a corresponds to the first component sidewall 26a, and has pixel values corresponding to a first center wavelength (e.g., 700 nm) output by the first sidewall illuminator 200a; a second or right sidewall image or sidewall image region 510b corresponds to the second component sidewall 26b, and has pixel values corresponding to a second center wavelength (e.g., 550 nm) output by the second sidewall illuminator 200b; a third or upper sidewall image or sidewall image region 510c corresponds to the third component sidewall 26c, and has pixel values corresponding to a third center wavelength (e.g., 600 nm) output by the third sidewall illuminator 200c; and a fourth or lower sidewall image or sidewall image region 510d corresponds to the fourth component sidewall 26d, and has pixel values corresponding to a fourth center wavelength (e.g., 450 nm) output by the fourth sidewall illuminator 200d.

When the component 20 is positioned at the centered sidewall inspection position, each component sidewall 26a-d can be illuminated by its corresponding sidewall illuminator 200a-d, and each component sidewall 26a-d can be simultaneously captured in a single image/as a single view (e.g., in a single image capture operation) by the color camera 400 to produce a wavelength segregated multi-sidewall image that can be analyzed to identify defects (e.g., micro-defects, such as micro-cracks) in each sidewall 26a-d by way of image processing operations. In general, with appropriate center wavelength separation or segregation between opposing or oppositely facing/oppositely directed sidewall illuminators 200a-d, the effects of extraneous sidewall illumination on any given sidewall image region 510a-d can be reduced or minimized. Moreover, by way of an appropriate calibration procedure prior to the initiation of sidewall inspection operations for a given type of component 20, the impact of extraneous sidewall illumination on pixel values corresponding to each sidewall image region 510a-d within the wavelength segregated multi-sidewall image 500 can be reduced, minimized, or effectively eliminated.

FIG. 6C is a schematic illustration of a first sidewall illuminator activation pattern corresponding to a wavelength segregated sidewall inspection calibration procedure in accordance with an embodiment of the present disclosure. In a first calibration operation, the first sidewall illuminator 200a is activated, while the other sidewall illuminators 200b-d are off; or at least, while the second sidewall illuminator 200b is off and at least one of the third and fourth sidewall illuminators 200c,d is off). For purpose of simplicity and to aid understanding, each of the second through fourth sidewall illuminators 200b-c are defined to be off during the first calibration operation. Bandwidth limited illumination having a first center wavelength output by the first sidewall illuminator 200a passes through the first sidewall beam splitter 210a, and is directed along optical paths parallel to the x axis toward the component 20. Some of such illumination is reflected by the first component sidewall 26a back to the first sidewall beam splitter 210a, which redirects this reflected sidewall illumination toward the image capture beam splitter 110. The image capture beam splitter's reflecting surface 112 subsequently redirects this first bandwidth limited illumination toward and into the lens assembly 300 and the image capture device 400, and a first calibration image of the first sidewall 26a under first bandwidth limited illumination conditions is captured. For instance, when the first bandwidth limited illumination corresponds to optical wavelengths of 700+/−30 nm, the first calibration image of the first sidewall 26a can be defined as a "pure red" image.

FIG. 6D is a schematic illustration of a second sidewall illuminator activation pattern corresponding to a wavelength segregated sidewall inspection calibration procedure in accordance with an embodiment of the present disclosure. In a second calibration operation, both of the first and second sidewall illuminators 200a,b, which are disposed opposite to or across from each other, are activated. For purpose of simplicity and to aid understanding, the third and fourth sidewall illuminators 200c,d are defined to be off during the second calibration operation. Because the first and second sidewall illuminators 200a,b are active during the second calibration operation, some of the first bandwidth limited illumination from the first sidewall illuminator 200a will be reflected by the first sidewall 26a back toward the first sidewall beam splitter 210a. Additionally, some of the second bandwidth limited illumination from the second sidewall illuminator 200b will not be reflected by the second sidewall 26b, but will instead travel past the component 20 to the first sidewall beam splitter 210a, thereby providing or contributing to extraneous second bandwidth limited sidewall illumination that will be present in a captured image of the first sidewall 26a, in addition to the first bandwidth limited illumination reflected from the first sidewall 26a. That is, the first sidewall beam splitter 210a redirects or reflects first bandwidth limited illumination reflected by the first sidewall 26a and extraneous second bandwidth limited illumination toward the image capture beam splitter 110, which redirects such first bandwidth limited illumination and extraneous second bandwidth limited illumination toward and to the lens assembly 300 and the image capture device 400. A second calibration image of the first sidewall 26a under first bandwidth limited illumination conditions plus extraneous second bandwidth limited illumination is then captured. For instance, when the first bandwidth limited illumination corresponds to optical wavelengths of 700+/−30 nm and the second bandwidth limited illumination corresponds to optical wavelengths of 550+/−30 nm, this second calibration image of the first sidewall 26a can be defined as a "pure red plus extraneous green" image.

Next, the first and second calibration images of the first sidewall 26a are processed, compared, and/or analyzed relative to each other to detect or determine the magnitude of an effect, if any, that the extraneous second bandwidth limited illumination in the second calibration image of the first sidewall 26a has relative to the first calibration image of the first sidewall 26, which excludes such extraneous sidewall illumination. For instance, in some embodiments, pixel values in the first calibration image are averaged, and pixel values in the second calibration image are averaged. Averaged pixel values corresponding to counterpart image locations in the first and second calibration images can be subtracted from each other to arrive at a first compensation factor that can be digitally applied (e.g., as a subtraction operation) to captured sidewall images or image regions 510a corresponding to the first sidewall 26a in association with component inspection operations. That is, the first compensation factor can be applied to (e.g., subtracted from) each pixel value within each first sidewall image region 510a of a wavelength segregated multi-sidewall image captured during actual component inspection operations. In other embodiments, pixel values in the first calibration image are directly subtracted from pixel values in the second calibration image, and the resulting difference or differential pixel values are averaged to arrive at a first compensation factor that can be digitally applied (e.g., as a subtraction operation) to captured sidewall image regions 510a corresponding to the first sidewall 26a in association with wavelength segregated component sidewall inspection operations. Depending upon embodiment details and/or the type of a component 20 or component sidewalls 26 under consideration, a compensation factor can be a positive value or a negative value, in a manner understood by one having ordinary skill in the relevant art.

Figure 6E:
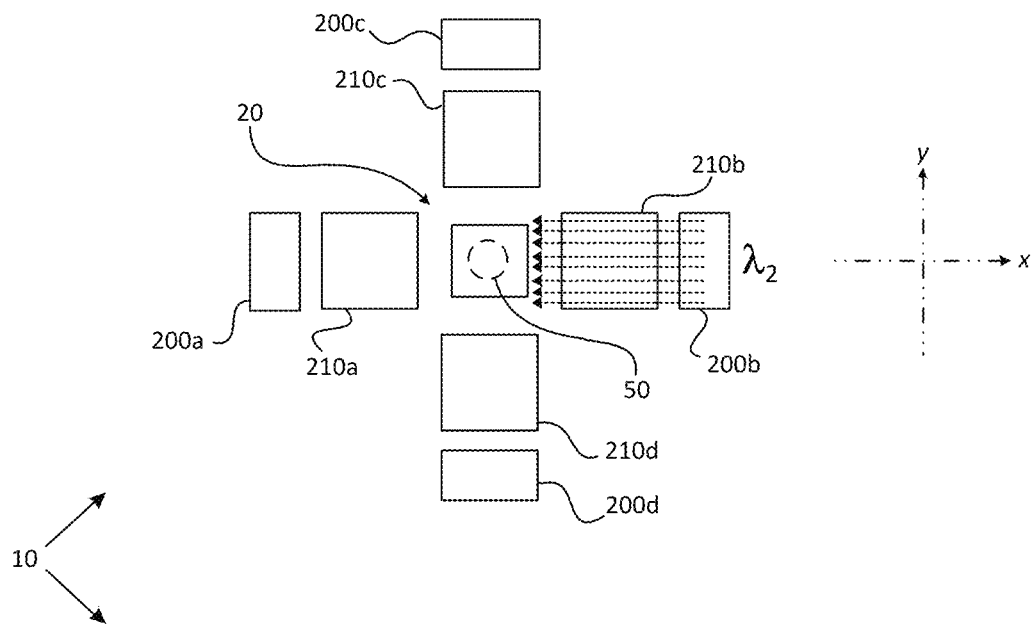
FIG. 6E is a schematic illustration of a third sidewall illuminator activation pattern corresponding to a wavelength segregated sidewall inspection calibration procedure in accordance with an embodiment of the present disclosure.
Figure 6F:
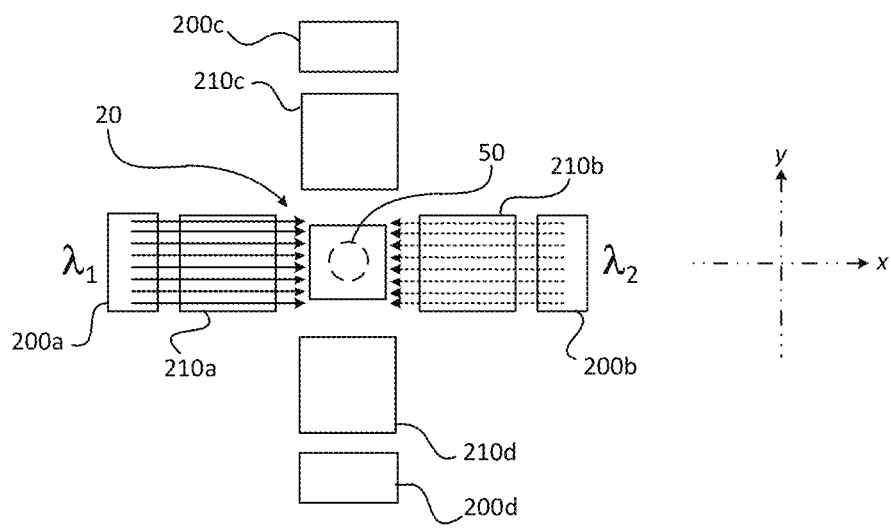
FIG. 6F is a schematic illustration of a fourth sidewall illuminator activation pattern corresponding to a wavelength segregated sidewall inspection calibration procedure in accordance with an embodiment of the present disclosure.

The foregoing types of calibration operations can subsequently performed to capture a third calibration image (e.g., a "pure green" image) of the second component sidewall 26b corresponding to the second bandwidth limited illumination alone, in a manner indicated in FIG. 6E; and a fourth calibration image (e.g., a "pure green plus extraneous red" image) of the second component sidewall 26b in a manner indicated in FIG. 6F. A second compensation factor, which can be applied to captured sidewall image regions 510b corresponding to the second sidewall 26b in association with wavelength segregated component sidewall inspection operations is then determined, for instance, in a manner indicated above.

Figure 6G:
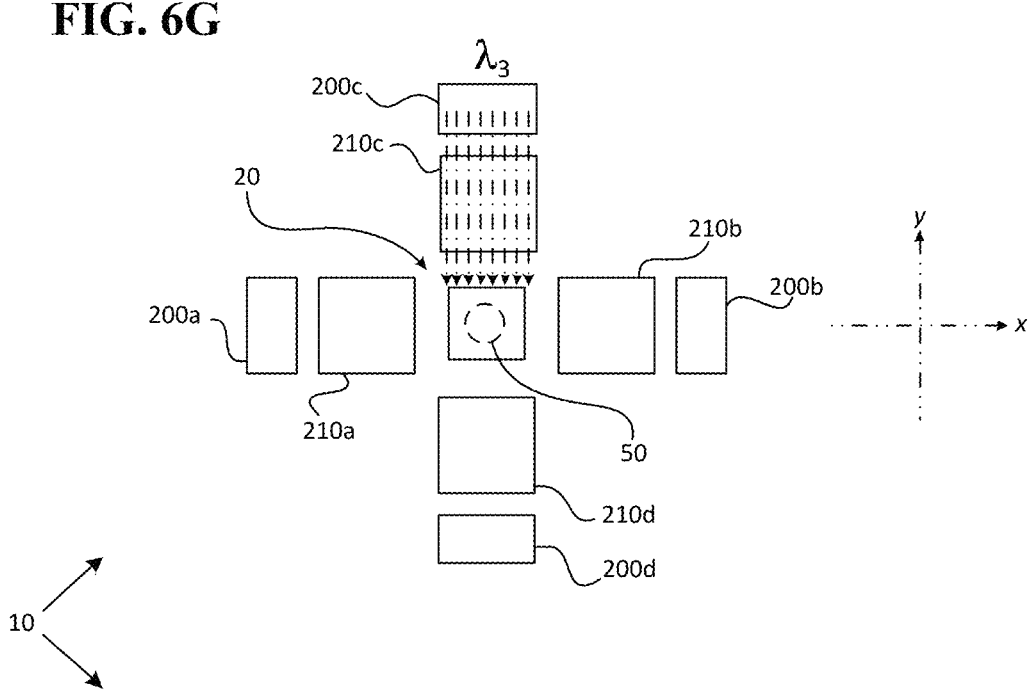
FIG. 6G is a schematic illustration of a fifth sidewall illuminator activation pattern corresponding to a wavelength segregated sidewall inspection calibration procedure in accordance with an embodiment of the present disclosure.
Figure 6H:
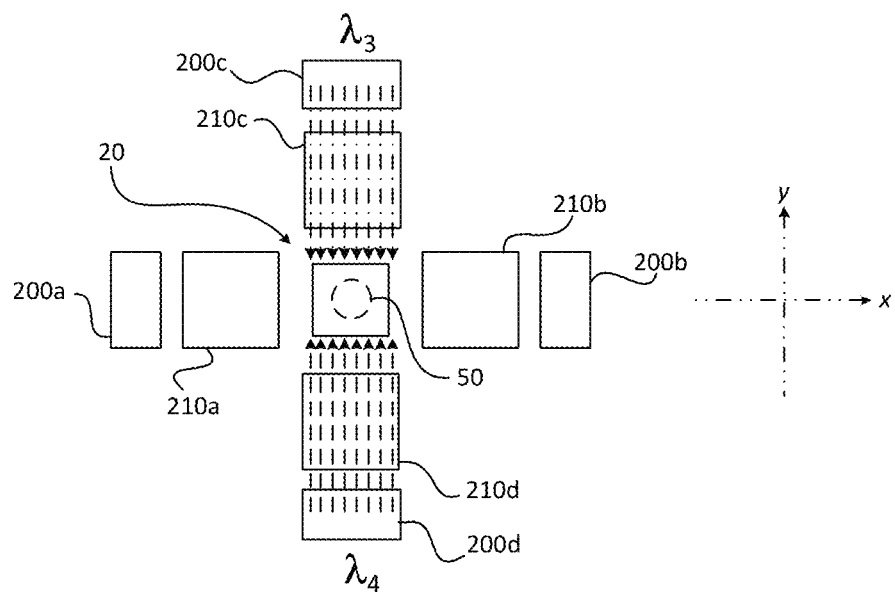
FIG. 6H is a schematic illustration of a sixth sidewall illuminator activation pattern corresponding to a wavelength segregated sidewall inspection calibration procedure in accordance with an embodiment of the present disclosure.
Figure 6K:
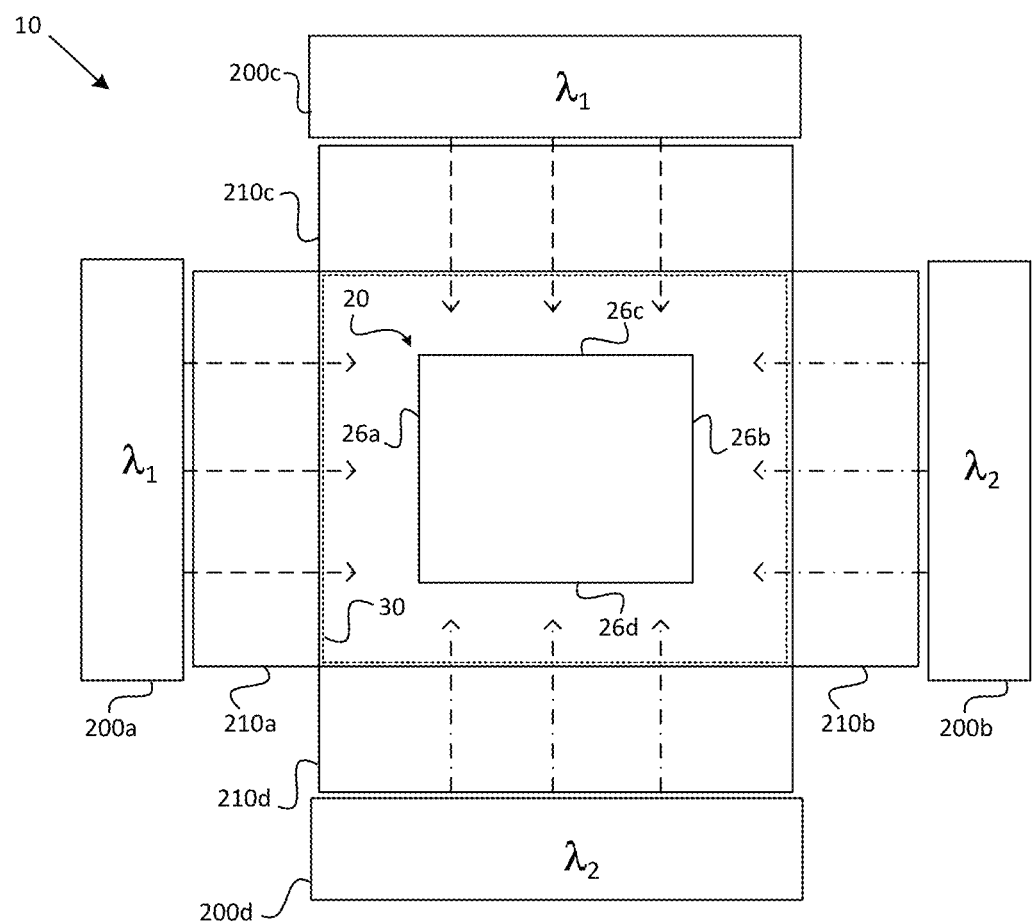
FIG. 6K is a schematic top view illustrating portions of an optical wavelength or bandwidth segregated sidewall inspection apparatus configured for performing an optical wavelength or bandwidth segregated sidewall inspection process or technique in accordance with an embodiment of the present disclosure.

Similarly, the above types of calibration operations can be performed to capture a fifth calibration image (e.g., a "pure orange" image) of the third component sidewall 26c corresponding to the third bandwidth limited illumination alone, in a manner indicated in FIG. 6G; and a sixth calibration image (e.g., a "pure orange plus extraneous blue" image) of the third component sidewall 26c in a manner indicated in FIG. 6H. A third compensation factor, which can be applied to captured sidewall image regions 510c corresponding to the third sidewall 26c in association with wavelength segregated component sidewall inspection operations is determined, for instance, in a manner indicated above.

Finally, the above types of calibration operations can be performed to capture a seventh calibration image (e.g., a "pure blue" image) of the fourth component sidewall 26d corresponding to the fourth bandwidth limited illumination alone, in a manner indicated in FIG. 6I; and an eighth calibration image (e.g., a "pure blue plus extraneous orange" image) of the fourth component sidewall 26d in a manner indicated in FIG. 6J. A fourth compensation factor, which can be applied to captured sidewall image regions 510d corresponding to the fourth sidewall 26d in association with wavelength segregated component sidewall inspection operations is determined, such as in a manner indicated above.

An individual having ordinary skill in the relevant art will recognize that some of the foregoing calibration operations can be combined, such as by way of selectively activating adjacent sidewall illuminators 200a,c/200b,d (or 200a,d/200b,c) at particular times. One having ordinary skill in the art will further recognize that compensation factors can be determined for a given type of component 20, and can be saved in a memory, database, and/or a data storage medium for later retrieval as part of an optical inspection recipe (e.g., a wavelength segregated component inspection recipe). An appropriate inspection recipe can be retrieved or loaded as part of an inspection setup procedure, in a manner readily understood by one having ordinary skill in the relevant art.

As indicated above, in addition or as an alternative to the foregoing, in several embodiments, individual opposing sidewall illuminators 200a-d are configured for outputting sidewall illumination having different optical center wavelengths or bandwidths relative to each other, while non-opposing sidewall illuminators 200a-d are configured for outputting sidewall illumination having identical, essentially identical, or overlapping optical center wavelengths or bandwidths relative to each other. Thus, when each sidewall illuminator 200a-d is active concurrent with each other sidewall illuminator 200a-d, sidewall illumination incident upon opposing component sidewalls 26a,b, 26c,d exhibits different optical center wavelengths or bandwidths. As a result, optical wavelength or bandwidth based digital discrimination or compensation operations can once again be performed upon a single captured image that includes image data which clearly represents or contains useful information corresponding to each component sidewall 26a-d, in order to compensate for or essentially eliminate "optical crosstalk" associated with opposing sidewall beam splitters 210a,b, 210c,d and their respective sidewall illuminators 200a,b, 200c,d.

FIG. 6K is a schematic top view illustrating portions of an optical wavelength or bandwidth segregated sidewall inspection apparatus 10 configured for performing an optical wavelength or bandwidth segregated sidewall inspection process or technique in accordance with another embodiment of the present disclosure. In such an embodiment, opposing sidewall illuminators 200a,b, 200c,d are configured for outputting sidewall illumination having different optical center wavelengths or bandwidths. Sidewall illumination traveling through opposing sidewall beam splitters 210a,b, 210c,d toward opposing component sidewalls 26a,b, 26c,d is bandwidth limited light (e.g., generally, narrow, narrow, or very narrow bandwidth light) having a distinct optical center frequency or wavelength. The bandwidth of each center wavelength can be approximately 30 nm (or less) around/about the center wavelength. Such sidewall illumination can be provided by way of LEDs having an appropriate wavelength output, and/or wavelength filters applied to broad spectrum illumination (e.g., white/substantially white light) produced by the sidewall illuminators 200a-d.

In a representative implementation, which includes four sidewall beam splitters 210a-d configured to receive sidewall illumination output by four corresponding sidewall illuminators 200a-d, the opposing first and second sidewall illuminators 200a,b are respectively configured for directly or essentially directly transmitting therethrough, without redirection, sidewall illumination having a first optical center wavelength $\lambda_1$ (e.g., red light centered at approximately 700 nm) and a second optical center wavelength $\lambda_2$ (e.g., blue light centered at approximately 450 nm); and the opposing third and fourth sidewall illuminators 200c,d are respectively configured for transmitting therethrough, without redirection, sidewall illumination having the first optical center wavelength $\lambda_1$ and the second optical center wavelength $\lambda_2$. Thus, the oppositely facing first and second component sidewalls 26a,b receive, by way of the first and second sidewall beam splitters 210a,b, incident sidewall illumination centered at the first optical wavelength $\lambda_1$ and the second optical wavelength $\lambda_2$, respectively; and the oppositely facing third and fourth component sidewalls 26c,d receive, by way of the third and fourth sidewall beam splitters 210c,d, incident sidewall illumination centered at the first optical wavelength $\lambda_1$ and the second optical wavelength $\lambda_2$, respectively.

Thus, each component sidewall 26a-d can be simultaneously illuminated such that oppositely facing component sidewalls 26a,b, 26c,d receive bandwidth limited light having distinct distinguishable optical center wavelengths $\lambda_1$ and $\lambda_2$. With respect to illumination traveling away from the component 20 and out of the sidewall inspection area 30 to the sidewall beam splitters 210a-d, any given sidewall beam splitter 210a-d receives (a) reflected sidewall illumination from its corresponding sidewall 26a-d at the same optical center wavelength $\lambda_1$ or $\lambda_2$ as was incident upon such sidewall 26a-d, and (b) non-reflected extraneous illumination that propagated across the sidewall inspection area 30, and which has a different center wavelength $\lambda_2$ or $\lambda_1$ than was incident upon its corresponding sidewall 26a-d.

During a single image capture operation, the color image capture device 400 can capture, as a single view, illumination that each sidewall beam splitter 210a-d has redirected towards the image capture beam splitter 110. The image capture device 400 correspondingly generates a single set of image data in which pixel data falling within or defining the image space representation of any given component sidewall 26a-d under consideration corresponds to one of the first and second optical center wavelengths $\lambda_1$ or $\lambda_2$; and pixel data falling outside of the image space boundaries of the component sidewall 26a-d under consideration corresponds to the other of the first and second optical center wavelengths $\lambda_2$ or $\lambda_1$. Moreover, pixel data falling within or defining the image space representation of any given pair or oppositely facing component sidewalls 26a-d corresponds to different optical center wavelengths, namely, $\lambda_1$ or $\lambda_2$. Thus, pixel data representing the first component sidewall 26a includes pixel values corresponding to the first optical center wavelength $\lambda_1$, but excludes or essentially excludes pixel values corresponding to the second optical center wavelength $\lambda_2$; and pixel data representing the second component sidewall 26b includes pixel values corresponding to the second optical center wavelength $\lambda_2$, but excludes or essentially excludes pixel values corresponding to the first optical center wavelength $\lambda_1$. Analogously pixel data representing the third component sidewall 26c includes pixel values corresponding to the first optical center wavelength $\lambda_1$, but excludes or essentially excludes pixel values corresponding to the second optical center wavelength $\lambda_2$; and pixel data representing the fourth component sidewall 26d includes pixel values corresponding to the second optical center wavelength $\lambda_2$, but excludes or essentially excludes pixel values corresponding to the first optical center wavelength $\lambda_1$.

Digital pixel filtering or wavelength compensation operations can be applied to the pixel data within different portions of the single set of image data (e.g., corresponding to different regions or quadrants in which sidewall beam splitters 210a-d reside in real/physical space) in association with or as part of an automated sidewall inspection process, thereby compensating for or effectively eliminating extraneous illumination or "optical crosstalk." Such digital pixel filtering or wavelength compensation operations can include pixel value subtraction operations performed upon each different portion of the single set of image data in which pixel values representing a specific component sidewall 26a-d exist (or should/are expected to exist), such that for each such portion of the single set of image data, pixel values corresponding to a set of optical wavelengths or an optical bandwidth associated with extraneous sidewall illumination peripheral to each component sidewall 26a-d are subtracted therefrom, effectively eliminating the effect(s) of "optical crosstalk." As set forth above, such extraneous illumination or "optical crosstalk" arises from the simultaneous transmission of incident sidewall illumination toward or generally toward oppositely facing component sidewalls 26a-d by way of oppositely positioned sidewall beam splitters 210a,b, 210c,d, but which is not reflected thereby and instead travels completely across the sidewall inspection area 30.

An individual having ordinary skill in the relevant art will understand that optical wavelength or bandwidth based calibration operations can be performed for an apparatus 10 such as that shown in FIG. 6K (e.g., if desired or required), in a manner analogous to that previously described above. An individual having ordinary skill in the relevant art will further understand that the simultaneous (a) provision of incident sidewall illumination to multiple component sidewalls 26a-d, (b) redirection of reflected sidewall illumination from multiple component sidewalls 26a-d, and/or (c) propagation of reflected sidewall illumination toward the image capture device 400 in a wavelength separated/segregated/specific manner (e.g., at different distinguishable optical center wavelengths or bandwidths) can occur by way of sidewall illuminators 200a-d configured for outputting illumination having distinct distinguishable optical center wavelengths or bandwidths, and/or the use of optical filters or coatings in the apparatus 10 (e.g., particular optical filters or coatings corresponding to particular sidewall beam splitters 210a-d).

Additional/Alternate Selectable Component Positioning and Inspection Configurations In various embodiments, the component holder 50 can additionally position a component 20 carried thereby at a second, upper, or front-surface-only inspection position along the z axis, such that the component's sidewalls 26a-d, and possibly the entire component 20 itself, reside above the set of sidewall beam splitters 210a-d. As a result, the component 20 is not an obstruction relative to light that travels along lateral optical paths between opposing sidewall beam splitters 210a,b, 210c,d.

More particularly, FIG. 7A illustrates a representative component positioning at a bottom-surface-only inspection position, in which the component 20 is disposed entirely above the set of sidewall beam splitters 210a-d. Brightfield illumination output by the brightfield illuminator 100 can travel upward to the component's bottom surface 24, and be reflected by the bottom surface 24 and structures carried thereby 28 in a downward direction toward the image capture beam splitter 110 to facilitate the capture of an image corresponding to the component's bottom surface 24. Brightfield illumination reaching any given sidewall beam splitter 210a-d is redirected thereby toward an opposite sidewall beam splitter 210a-d. Because the component 20 is disposed above the sidewall beam splitters 210a-d, the component sidewalls 26a-d are not imaged, as indicated in the accompanying image in FIG. 7A, which includes pixels corresponding to features associated with the component's front surface 20 but which lacks pixels corresponding to structural aspects of the component's sidewalls 26a-d.

As indicated in FIG. 7B, the component holder 50 can additionally or alternatively position the component 20 at a sidewall inspection position (e.g., at least one sidewall inspection position within the sidewall inspection area 30), such that brightfield or darkfield illumination output by the brightfield illuminator 100 or the darkfield illuminator 120, respectively, can travel upwardly to the component's bottom surface 24 and structures 28 carried thereby, and be reflected therefrom in a downward direction toward the image capture beam splitter 110 to facilitate the capture of an image corresponding to the component's bottom surface 24. Brightfield or darkfield illumination can additionally travel to the sidewall beam splitters 210a-d, whereupon it is redirected along travel paths toward the component's sidewalls 26a-d. A portion of such illumination will be reflected by the component's sidewalls 26a-d back toward the sidewall beam splitters 210a-d, which redirects such illumination in a downward direction toward the image capture beam splitter 110 to facilitate the capture of component sidewall images. A representative captured image in FIG. 7B includes pixels corresponding to structures associated with the component's front surface 20, as well as pixels corresponding to structural aspects of the component's sidewalls 26a-d.

Finally, as indicated in FIG. 7C, while at the sidewall inspection position, with the brightfield and darkfield illuminators 100, 110 inactive or off, some or each of the sidewall illuminators 200a-d can be activated, such that component sidewall images can be captured in a manner essentially identical or analogous to one or more manners described above, as also indicated by the representative captured image in FIG. 7C.

In various embodiments, a vertical or z axis difference between the bottom-surface-only inspection position and the sidewall inspection position(s) can be selected or determined such that an overall optical path length corresponding to an in-focus image of the component's bottom surface 24 which is captured when the component resides at the bottom-surface-only inspection position is equal to an optical path length corresponding to an in-focus image of the component's sidewalls 26 when the component 20 resides at the sidewall inspection position(s). For instance, when a component 20 resides at the bottom-surface-only inspection position, the vertical or z axis optical path length between the bottom surface 24 of the component 20 or the front surface image plane 410 and the image capture beam splitter's reflecting surface 112 can be established such that it equals the lateral optical path length plus vertical optical path length along which light reflected from component sidewalls 26a-d travels in reaching the image capture beam splitter's reflecting surface 112. As a result, no change in focus or lens assembly adjustment is required whether the component 20 is positioned at the bottom-surface-only inspection position or the sidewall inspection position(s), and no time or essentially/nearly no time is lost because in order to position the component 20 at the sidewall inspection position(s), the component 20 would have to arrive at or near the bottom-surface-only inspection before being plunged to the sidewall inspection position(s).

Figure 7D:
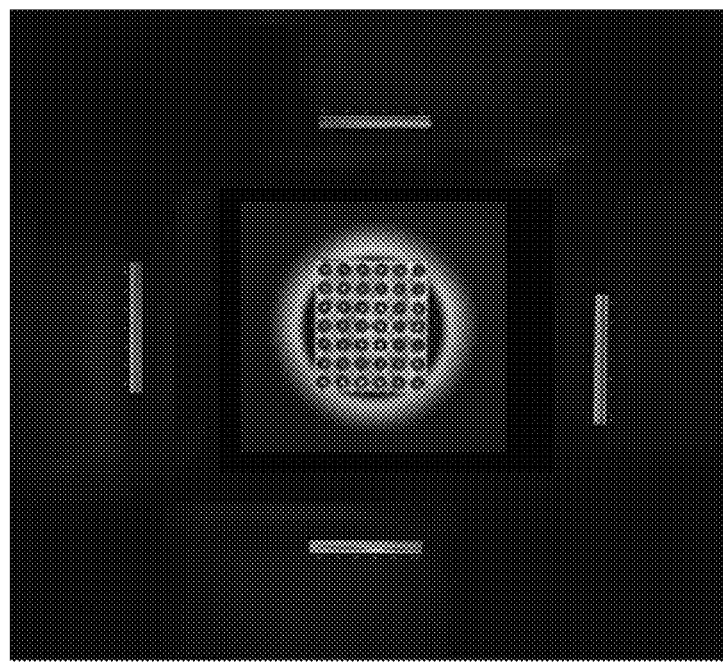
FIG. 7D is a representative composite five side inspection image that includes a central bottom surface image or image region and four peripheral sidewall images or image regions disposed about the central bottom surface image region in accordance with an embodiment of the present disclosure.

In addition to the foregoing, a five side composite image can be generated to facilitate front surface and sidewall inspection. The five side composite image can be generated by a digital stitching operation, for instance, by way of digitally stitching together a central (e.g., bottom surface) image region corresponding to FIG. 7A with sidewall image regions corresponding to one or more multi-sidewall images, or sidewall image regions 510a-d corresponding to a wavelength segregated multi-sidewall image. A representative five side composite image is shown in FIG. 7D.

Aspects of particular embodiments of the present disclosure address at least one aspect, problem, limitation, and/or disadvantage associated with exiting optical inspection systems that can capture images of component sidewalls. While features, aspects, and/or advantages associated with certain embodiments have been described in the disclosure, other embodiments may also exhibit such features, aspects, and/or advantages, and not all embodiments need necessarily exhibit such features, aspects, and/or advantages to fall within the scope of the disclosure. It will be appreciated by a person of ordinary skill in the art that several of the above-disclosed systems, components, processes, or alternatives thereof, may be desirably combined into other different systems, components, processes, and/or applications. In addition, various modifications, alterations, and/or improvements may be made to various embodiments that are disclosed by a person of ordinary skill in the art within the scope of the present disclosure.

The invention claimed is:

1. An apparatus configured for inspecting component surfaces including component sidewalls, the apparatus comprising:
   a set of sidewall illuminators configured to output sidewall illumination;
   a set of sidewall beam splitters configured for:
      (a) receiving the sidewall illumination output by the set of sidewall illuminators;
      (b) transmitting said sidewall illumination output by the set of sidewall illuminators through the set of sidewall beam splitters, such that at least some the sidewall illumination is incident on component sidewalls when a component is positioned within a sidewall inspection area at a sidewall inspection position at which the component sidewalls obstruct at least some optical paths between individual sidewall beam splitters within the set of sidewall beam splitters;
      (c) receiving reflected sidewall illumination from component sidewalls when the component is positioned at the sidewall inspection position;
      (d) redirecting the reflected sidewall illumination along optical paths corresponding to a lens assembly and an image capture device; and
   a processing unit to selectively activate at least one or a combination of
      (i) a single or a pair of adjacent or opposing sidewall illuminators for capturing images of one or a pair of adjacent or opposing side walls while the other sidewall illuminators not selected, are in a non-activated state, and
      (ii) a distinct and separate center wavelength or bandwidth illumination of individual ones of the sidewall illuminators for capturing individual images of a selected side wall or simultaneously capturing images of more than one sidewalls of the component side walls.

2. The apparatus of claim 1, wherein the set of sidewall illuminators, the set of sidewall beam splitters and the image capture device is further configured for capturing images of a component bottom surface and/or images of component sidewalls.

3. The apparatus of claim 1, wherein the set of sidewall illuminators includes at least one pair of sidewall illuminators in which two sidewall illuminators are oppositely disposed relative to each other with respect to the sidewall inspection position.

4. The apparatus of claim 1, wherein the set of sidewall beam splitters includes at least one pair of sidewall beam splitters that are oppositely disposed on different sides of the sidewall inspection area relative to an axis defined through the sidewall inspection area.

5. The apparatus of claim 4, wherein the at least one pair of oppositely disposed sidewall beam splitters includes a first sidewall beam splitter and a second sidewall beam splitter, wherein the first sidewall beam splitter is configured for transmitting first sidewall illumination having a first optical wavelength or a first optical bandwidth therethrough and the second sidewall beam splitter is configured for transmitting second sidewall illumination having a distinct second optical wavelength or a second optical bandwidth therethrough, wherein the first sidewall beam splitter is configured for receiving and redirecting each of first reflected sidewall illumination from a first component sidewall and second extraneous sidewall illumination transmitted through the second sidewall beam splitter that has traveled across the sidewall inspection area, and wherein the second sidewall beam splitter is configured for receiving and redirecting each of second reflected sidewall illumination from a second component sidewall and first extraneous sidewall illumination transmitted through the first sidewall beam splitter that has traveled across the sidewall inspection area.

6. The apparatus of claim 1, wherein
the image capture device configured for
   (a) capturing in a single image capture operation a single image comprising a first image region corresponding to the first reflected sidewall illumination and the second extraneous sidewall illumination, and a second image region corresponding to the second reflected sidewall illumination and the first extraneous sidewall illumination, and
   (b) generating image data corresponding to the single image; and
the processing unit is further configured for processing the image data such that pixel values corresponding to the second extraneous sidewall illumination are digitally filtered from image data corresponding to the first image region, and pixel values corresponding to the first extraneous sidewall illumination are digitally filtered from image data corresponding to the second image region.

7. The apparatus of claim 1, wherein the set of sidewall illuminators includes a plurality of sidewall illuminators in which
   (a) each sidewall illuminator outputs illumination at the same optical center wavelength or bandwidth, or
   (b) a first subset of sidewall illuminators outputs illumination having a distinct optical center wavelength or bandwidth relative to illumination output by a second subset of sidewall illuminators.

8. The apparatus of claim 1, wherein particular subsets of sidewall illuminators within the set of sidewall illuminators are selectively activatable for outputting sidewall illumination while other subsets of sidewall illuminators within the set of sidewall illuminators remain inactive.

9. The apparatus of claim 1, wherein the brightfield illuminator and/or darkfield illuminator is configured for selectively directing illumination toward a bottom surface or the bottom surface and sidewalls of a component positioned at the sidewall inspection position, wherein the component sidewalls extend between the bottom surface and a top surface of the component.

10. The apparatus of claim 9, further comprising an image capture beam splitter configured for
   (a) receiving illumination output by the brightfield illuminator and passing brightfield illumination therethrough;
   (b) receiving reflected brightfield and/or darkfield illumination from the component bottom surface and/or component sidewalls;
   (c) receiving reflected sidewall illumination from component sidewalls which has been redirected by the set of sidewall beam splitters; and
   (d) redirecting received reflected illumination corresponding to (b) and (c) along optical paths toward a lens assembly.

11. The apparatus of claim 1, wherein the image capture device includes a monochrome image sensor or a color image sensor.

12. The apparatus of claim 11, further comprising a component holder configured for selectively positioning a component at the sidewall inspection position or a bottom-surface-only inspection position at which component obstruction of optical paths between each sidewall beam splitter is avoided.

13. The apparatus of claim 12, wherein the component holder is configured for selectively positioning a component held thereby at multiple sidewall inspection positions within the sidewall inspection area, including a first sidewall inspection position at which a component center point is positioned closer to a first subset of sidewall beam splitters than a distinct second subset of sidewall beam splitters, and a second sidewall inspection position at which the component center point is positioned closer to the second subset of sidewall beam splitters than the first set of sidewall beam splitters.

14. The apparatus of claim 1, wherein the processing unit is configured for selectively positioning the component at one or more inspection positions within the inspection area to capture one or more images of component surfaces by way of the image capture device.

15. A method for component inspection, comprising:
providing a set of sidewall illuminators configured for outputting sidewall illumination at one or more center wavelengths or wavelength ranges;
providing a set of sidewall beam splitters configured for receiving the sidewall illumination output by the set of sidewall illuminators;
disposing a component at a first sidewall inspection position such that component sidewalls at least partially obstruct at least some optical paths between individual sidewall beam splitters within the set of sidewall beam splitters;
directing sidewall illumination output by the set of sidewall illuminators toward component sidewalls by way of passing sidewall illumination received by the set of sidewall beam splitters therethrough;
receiving sidewall illumination output by the set of sidewall beam splitters at a plurality of component sidewalls while the component resides at the first sidewall inspection position;
receiving reflected sidewall illumination from the plurality of component sidewalls at the plurality of sidewall beam splitters;
redirecting reflected sidewall illumination received by the plurality of sidewall beam splitters along optical paths corresponding to a single image capture device; and
selectively activating at least one or a combination of
   (i) a single or a pair of adjacent or opposing sidewall illuminators for capturing images of one or a pair of adjacent or opposing side walls while the other sidewall illuminators not selected, are in a non-activated state, and (ii) a distinct and separate center wavelength or bandwidth illumination of individual ones of the sidewall illuminators for capturing individual images of a selected side wall or simultaneously capturing images of more than one sidewalls of the component side walls.

16. The method of claim 15, further comprising selectively directing sidewall illumination toward a first subset of component sidewalls while avoiding directing sidewall illumination toward a second subset of component sidewalls during a first image capture operation.

17. The method of claim 16, further comprising selectively directing sidewall illumination toward the second subset of component sidewalls while avoiding directing sidewall illumination toward the first subset of component sidewalls during a second image capture operation.

18. The method of claim 15, further comprising:
capturing a first image including pixel regions corresponding to a first subset of component sidewalls; and
capturing a second image including pixel regions corresponding to a second subset of component sidewalls.

19. The method of claim 18, further comprising creating a composite image by way of digitally stitching together portions of the first image corresponding to the first subset of component sidewalls and portions of the second image corresponding to the second subset of component sidewalls.

20. The method of claim 18, wherein capturing the first image occurs while the component is disposed at the first sidewall inspection position within a sidewall inspection area definable between the set of sidewall beam splitters, and capturing the second image occurs while the component is disposed at a distinct second sidewall inspection position within the sidewall inspection area.

21. The method of claim 20, wherein a center point of the component is closer to a first subset of sidewall beam splitters when the component is disposed at the first sidewall inspection position, and the center point of the component is closer to a distinct second subset of sidewall beam splitters when the component is disposed at the second sidewall inspection position.

22. The method of claim 15, wherein the sidewall illumination comprises first sidewall illumination and second sidewall illumination, and the reflected sidewall illumination comprises first reflected sidewall illumination and second reflected sidewall illumination, and wherein the first sidewall illumination and the second sidewall illumination exhibit different bandwidth limited optical wavelength ranges, and/or the first reflected sidewall illumination and the second reflected sidewall illumination exhibit different bandwidth limited optical wavelength ranges.

23. The method of claim 22, further comprising capturing as a single view an image including a plurality of distinct pixel regions, each pixel region corresponding to a distinct component sidewall, each pixel region corresponding to one of at least two distinct bandwidth limited optical wavelength ranges.

24. The method of claim 23, further comprising performing a wavelength segregated calibration procedure prior to capturing the image, the wavelength segregated calibration procedure determining at least one calibration factor that can be applied to a pixel region corresponding to a particular component sidewall to effectively eliminate an effect of extraneous sidewall illumination in the captured image.

25. The method of claim 15, further comprising:
capturing at least one image including pixel regions corresponding to at least two component sidewalls while the component resides at the sidewall inspection position;
displacing the component to a bottom-surface-only inspection position at which component obstruction of optical paths between each sidewall beam splitter is avoided;
directing brightfield and/or darkfield illumination toward a bottom surface of the component while the component resides at the bottom-surface-only inspection position; and
capturing an image corresponding to the bottom surface of the component.

26. A method for inspecting a component having a plurality of sidewalls including a first component sidewall and a second component sidewall that face an opposite direction relative to each other along a first axis, the method comprising:
positioning the component at a sidewall inspection position within a sidewall inspection area between a plurality of sidewall beam splitters including a first sidewall beam splitter and a second sidewall beam splitter that are disposed on opposite sides of the sidewall inspection area along the first axis;
simultaneously transmitting sidewall illumination through the plurality of sidewall beam splitters such that the first component sidewall and the second component sidewall receive first incident sidewall illumination and second incident sidewall illumination thereon, respectively, at different optical center wavelengths or different optical bandwidths;
receiving at the first sidewall beam splitter
(a) first reflected sidewall illumination traveling away from the first component sidewall after first incident sidewall illumination arrival thereon and reflection therefrom, and
(b) second extraneous sidewall illumination that has been transmitted through the second sidewall beam splitter across the sidewall inspection area; receiving at the second sidewall beam splitter
(c) second reflected sidewall illumination traveling away from the second component sidewall after second incident sidewall illumination arrival upon and reflection therefrom, and
(d) first extraneous sidewall illumination that has been transmitted through the first sidewall beam splitter across the sidewall inspection area;
redirecting each of the first reflected sidewall illumination, the second extraneous sidewall illumination, the second reflected sidewall illumination, and the first extraneous sidewall illumination toward a single image capture device;
capturing in a single image capture operation as a single image the first reflected sidewall illumination and the second extraneous sidewall illumination as a first region of the single image, and the second reflected sidewall illumination and the first extraneous sidewall illumination as a second region of the single image;
generating image data corresponding to the single image; and
processing the image data to digitally filter pixel values corresponding to the second extraneous sidewall illumination from the first region of the single image, and the first extraneous sidewall illumination from the second region of the single image.

27. The apparatus of claim 1, wherein the captured images of the selected individual illuminated side walls or images of more than one sidewalls are compared relative to each other to eliminate the effects of extraneous sidewall illumination.

28. The apparatus of claim 27, wherein comparing the captured images relative to each other comprising detecting and/or determining the magnitude of an effect for defect and/or image compensation.

* * * * *